United States Patent [19]
Gregory

[11] Patent Number: 5,876,974
[45] Date of Patent: *Mar. 2, 1999

[54] **METHOD FOR PRODUCING DNA ENCODING CYSTIC FIBROSIS TRANSMEMBRANE CONDUCTANCE REGULATOR (CFTR) PROTEIN IN *E. COLI***

[75] Inventor: Richard J. Gregory, Carlsbad, Calif.

[73] Assignee: Genzyme Corporation, Framingham, Mass.

[*] Notice: The terminal 3 months of this patent has been disclaimed.

[21] Appl. No.: 298,522

[22] Filed: Aug. 30, 1994

Related U.S. Application Data

[63] Continuation of Ser. No. 87,132, Jul. 2, 1993, which is a continuation of Ser. No. 613,592, Nov. 15, 1990, abandoned, which is a continuation-in-part of Ser. No. 589,295, Sep. 27, 1990, abandoned, which is a continuation-in-part of Ser. No. 488,307, Mar. 5, 1990, abandoned.

[51] Int. Cl.$^6$ .......................... C12P 19/34; C12N 15/10; C07H 17/00; C07K 14/435
[52] U.S. Cl. ................... 435/91.1; 435/320.1; 536/23.1; 530/350
[58] Field of Search ............... 536/23.1, 23.72; 435/240.1, 320.1, 91.1; 530/350

[56] References Cited

U.S. PATENT DOCUMENTS

| 4,322,274 | 3/1982 | Wilson et al. |
|---|---|---|
| 5,240,846 | 8/1993 | Collins et al. ........................ 435/240.1 |

FOREIGN PATENT DOCUMENTS

| WO 91/002796 | 3/1991 | WIPO . |
|---|---|---|
| WO 91/10735 | 7/1991 | WIPO . |
| WO 92/05252 | 4/1992 | WIPO . |
| WO 92/05273 | 4/1992 | WIPO . |

OTHER PUBLICATIONS

Stenesh, 1989 Dictionary of Biochemistry and Molecular Biology 2nd Edition John Wiley & Sons, New York, pp. 241 and 490.
Ledley et al. 1991. Human Gene Therapy 2:77–83.
Gutierrez et al. 1992 Lancet 339:715–721.
Drumm et al 1990 Cell 62:1227–1233.
Rich et al 1990 Nature:347: 358–363.
Smith 1992 Ann. Reports in Med. Chem 27:235–243.
J.H. Chen et al., "A cAMP–Regulated Chloride Channel in Lymphocytes That is Affected in Cystic Fibrosis", *Science*, 243, 1989, pp. 657–660.
J. M. Rommens et al., "Identification of the Cystic Fibrosis Gene: Chromosome Walking and Jumping", *Science*, 245, 1989, pp. 1059–1065.
B–S. Kerem et al., "Identification of the Cystic Fibrosis Gene: Genetic Analysis", *Science*, 245, 1989, pp. 1073–1080.
J. Riordan et al., "Identification of the Cystic Fibrosis Gene: Cloning and Characterization of Complementary DNA", *Science*, 245, 1989, pp. 1066–1073.
R.J. Gregory et al., "Expression and Characterization of the Cystic Fibrosis Transmembrane Conductance Regulator", *Nature*, 347, Sep. 27, 1990, pp. 382–386.
M. Drumm et al., "The Full Length CFTR cDNA is Toxic in Bacteria", *Pediatric Pulmonology*, Supplement 5 (Abstracts), Oct. 1990, Abstract No. 8, p. 189.
S.H. Cheng et al., "Defective Intracellular Transport and Processing of CFTR Is the Molecular Basis of Most Cystic Fibrosis", *Cell*, 63, 1990, pp. 827–834.
L–C. Tsui. "Probing the Basic Defect in Cystic Fibrosis", *Current Opinion in Genetics and Development*, 1, 1991, pp. 4–10.
J. R. Dorin et al., "A Clue to the Basic Defect in Cystic Fibrosis from Cloning the CF Antigen Gene", *Nature*, 326, 1987, pp. 614–617.
J.A. Dodge, "Implications of the New Genetics for Screening for Cystic Fibrosis", *The Lancet*, issue of Sep. 17, 1988, pp. 672–674.

*Primary Examiner*—Karen C. Carlson
*Attorney, Agent, or Firm*—Baker & Botts, L.L.P

[57] ABSTRACT

A pharmaceutical composition comprising a vector itself comprising a purified and isolated DNA sequence consisting essentially of a DNA sequence encoding a polypeptide having an amino acid sequence sufficiently duplicative of CFTR to allow possession of the biological property of correction of a defect in epithelial cell anion channel regulation.

8 Claims, 23 Drawing Sheets

PARTIAL cDNA CLONES OF THE CFTR GENE

```
  1  AATTGGAAGCAAATGACATCACAGCAGGTCAGAGAAAAAGGG   42
 43  TTGAGCGGCAGGCACCCAGAGTAGTAGGTCTTTGGCATTAGG   84
 85  AGCTTGAGCCCAGACGGCCCTAGCAGGGACCCCAGCGCCCGA  126

1          MetGlnArgSerProLeuGluLysAlaSerValVal   12
127  GAGACCATGCAGAGGTCGCCTCTGGAAAAGGCCAGCGTTGTC  168

13  SerLysLeuPhePheSerTrpThrArgProIleLeuArgLys   26
169  TCCAAACTTTTTTTCAGCTGGACCAGACCAATTTTGAGGAAA  210

27  GlyTyrArgGlnArgLeuGluLeuSerAspIleTyrGlnIle   40
211  GGATACAGACAGCGCCTGGAATTGTCAGACATATACCAAATC  252

41  ProSerValAspSerAlaAspAsnLeuSerGluLysLeuGlu   54
253  CCTTCTGTTGATTCTGCTGACAATCTATCTGAAAAATTGGAA  294

55  ArgGluTrpAspArgGluLeuAlaSerLysLysAsnProLys   68
295  AGAGAATGGGATAGAGAGCTGGCTTCAAAGAAAAATCCTAAA  336

69  LeuIleAsnAlaLeuArgArgCysPhePheTrpArgPheMet   82
337  CTCATTAATGCCCTTCGGCGATGTTTTTTCTGGAGATTTATG  378

83  PheTyrGlyIlePheLeuTyrLeuGlyGluValThrLysAla   96
379  TTCTATGGAATCTTTTTATATTTAGGGGAAGTCACCAAAGCA  420

97  ValGlnProLeuLeuLeuGlyArgIleIleAlaSerTyrAsp  110
421  GTACAGCCTCTCTTACTGGGAAGAATCATAGCTTCCTATGAC  462

111  ProAspAsnLysGluGluArgSerIleAlaIleTyrLeuGly  124
463  CCGGATAACAAGGAGGAACGCTCTATCGCGATTTATCTAGGC  504

125  IleGlyLeuCysLeuLeuPheIleValArgThrLeuLeuLeu  138
505  ATAGGCTTATGCCTTCTCTTTATTGTGAGGACACTGCTCCTA  546

139  HisProAlaIlePheGlyLeuHisHisIleGlyMetGlnMet  152
547  CACCCAGCCATTTTTGGCCTTCATCACATTGGAATGCAGATG  588

153  ArgIleAlaMetPheSerLeuIleTyrLysLysThrLeuLys  166
589  AGAATAGCTATGTTTAGTTTGATTTATAAGAAGACTTTAAAG  630

167  LeuSerSerArgValLeuAspLysIleSerIleGlyGlnLeu  180
631  CTGTCAAGCCGTGTTCTAGATAAAATAAGTATTGGACAACTT  672

181  ValSerLeuLeuSerAsnAsnLeuAsnLysPheAspGluGly  194
673  GTTAGTCTCCTTTCCAACAACCTGAACAAATTTGATGAAGGA  714
```

FIG. 14A

| | | |
|---|---|---|
| 195 | LeuAlaLeuAlaHisPheValTrpIleAlaProLeuGlnVal | 208 |
| 715 | CTTGCATTGGCACATTTCGTGTGGATCGCTCCTTTGCAAGTG | 756 |
| 209 | AlaLeuLeuMetGlyLeuIleTrpGluLeuLeuGlnAlaSer | 222 |
| 757 | GCACTCCTCATGGGGCTAATCTGGGAGTTGTTACAGGCGTCT | 798 |
| 223 | AlaPheCysGlyLeuGlyPheLeuIleValLeuAlaLeuPhe | 236 |
| 799 | GCCTTCTGTGGACTTGGTTTCCTGATAGTCCTTGCCCTTTTT | 840 |
| 237 | GlnAlaGlyLeuGlyArgMetMetMetLysTyrArgAspGln | 250 |
| 841 | CAGGCTGGGCTAGGGAGAATGATGATGAAGTACAGAGATCAG | 882 |
| 251 | ArgAlaGlyLysIleSerGluArgLeuValIleThrSerGlu | 264 |
| 883 | AGAGCTGGGAAGATCAGTGAAAGACTTGTGATTACCTCAGAA | 924 |
| 265 | MetIleGluAsnIleGlnSerValLysAlaTyrCysTrpGlu | 278 |
| 925 | ATGATTGAAAATATCCAATCTGTTAAGGCATACTGCTGGGAA | 966 |
| 279 | GluAlaMetGluLysMetIleGluAsnLeuArgGlnThrGlu | 292 |
| 967 | GAAGCAATGGAAAAAATGATTGAAAACTTAAGACAAACAGAA | 1008 |
| 293 | LeuLysLeuThrArgLysAlaAlaTyrValArgTyrPheAsn | 306 |
| 1009 | CTGAAACTGACTCGGAAGGCAGCCTATGTGAGATACTTCAAT | 1050 |
| 307 | SerSerAlaPhePhePheSerGlyPhePheValValPheLeu | 320 |
| 1051 | AGCTCAGCCTTCTTCTTCTCAGGGTTCTTTGTGGTGTTTTA | 1092 |
| 321 | SerValLeuProTyrAlaLeuIleLysGlyIleIleLeuArg | 334 |
| 1093 | TCTGTGCTTCCCTATGCACTAATCAAAGGAATCATCCTCCGG | 1134 |
| 335 | LysIlePheThrThrIleSerPheCysIleValLeuArgMet | 348 |
| 1135 | AAAATATTCACCACCATCTCATTCTGCATTGTTCTGCGCATG | 1176 |
| 349 | AlaValThrArgGlnPheProTrpAlaValGlnThrTrpTyr | 362 |
| 1177 | GCGGTCACTCGGCAATTTCCCTGGGCTGTACAAACATGGTAT | 1218 |
| 363 | AspSerLeuGlyAlaIleAsnLysIleGlnAspPheLeuGln | 376 |
| 1219 | GACTCTCTTGGAGCAATAAACAAAATACAGGATTTCTTACAA | 1260 |
| 377 | LysGlnGluTyrLysThrLeuGluTyrAsnLeuThrThrThr | 390 |
| 1261 | AAGCAAGAATATAAGACATTGGAATATAACTTAACGACTACA | 1302 |
| 391 | GluValValMetGluAsnValThrAlaPheTrpGluGluGly | 404 |
| 1303 | GAAGTAGTGATGGAGAATGTAACAGCCTTCTGGGAGGAGGGA | 1344 |
| 405 | PheGlyGluLeuPheGluLysAlaLysGlnAsnAsnAsnAsn | 418 |
| 1345 | TTTGGGGAATTATTTGAGAAAGCAAAACAAAACAATAACAAT | 1386 |

FIG. 14B

| | | |
|---|---|---|
| 419 | ArgLysThrSerAsnGlyAspAspSerLeuPhePheSerAsn | 432 |
| 1387 | AGAAAAACTTCTAATGGTGATGACAGCCTCTTCTTCAGTAAT | 1428 |
| 433 | PheSerLeuLeuGlyThrProValLeuLysAspIleAsnPhe | 446 |
| 1429 | TTCTCACTTCTTGGTACTCCTGTCCTGAAAGATATTAATTTC | 1470 |
| 447 | LysIleGluArgGlyGlnLeuLeuAlaValAlaGlySerThr | 460 |
| 1471 | AAGATAGAAAGAGGACAGTTGTTGGCGGTTGCTGGATCCACT | 1512 |
| 461 | GlyAlaGlyLysThrSerLeuLeuMetMetIleMetGlyGlu | 474 |
| 1513 | GGAGCAGGCAAGACTTCACTTCTAATGATGATTATGGGAGAA | 1554 |
| 475 | LeuGluProSerGluGlyLysIleLysHisSerGlyArgIle | 488 |
| 1555 | CTGGAGCCTTCAGAGGGTAAAATTAAGCACAGTGGAAGAATT | 1596 |
| 489 | SerPheCysSerGlnPheSerTrpIleMetProGlyThrIle | 502 |
| 1597 | TCATTCTGTTCTCAGTTTTCCTGGATTATGCCTGGCACCATT | 1638 |
| 503 | LysGluAsnIleIlePheGlyValSerTyrAspGluTyrArg | 516 |
| 1639 | AAAGAAAATATCATCTTTGGTGTTTCCTATGATGAATATAGA | 1680 |
| 517 | TyrArgSerValIleLysAlaCysGlnLeuGluGluAspIle | 530 |
| 1681 | TACAGAAGCGTCATCAAAGCATGCCAACTAGAAGAGGACATC | 1722 |
| 531 | SerLysPheAlaGluLysAspAsnIleValLeuGlyGluGly | 544 |
| 1723 | TCCAAGTTTGCAGAGAAAGACAATATAGTTCTTGGAGAAGGT | 1764 |
| 545 | GlyIleThrLeuSerGlyGlyGlnArgAlaArgIleSerLeu | 558 |
| 1765 | GGAATCACACTGAGTGGAGGTCAACGAGCAAGAATTTCTTTA | 1806 |
| 559 | AlaArgAlaValTyrLysAspAlaAspLeuTyrLeuLeuAsp | 572 |
| 1807 | GCAAGAGCAGTATACAAAGATGCTGATTTGTATTTATTAGAC | 1848 |
| 573 | SerProPheGlyTyrLeuAspValLeuThrGluLysGluIle | 586 |
| 1849 | TCTCCTTTTGGATACCTAGATGTTTTAACAGAAAAAGAAATA | 1890 |
| 587 | PheGluSerCysValCysLysLeuMetAlaAsnLysThrArg | 600 |
| 1891 | TTTGAAAGCTGTGTCTGTAAACTGATGGCTAACAAAACTAGG | 1932 |
| 601 | IleLeuValThrSerLysMetGluHisLeuLysLysAlaAsp | 614 |
| 1933 | ATTTTGGTCACTTCTAAAATGGAACATTTAAAGAAAGCTGAC | 1974 |
| 615 | LysIleLeuIleLeuHisGluGlySerSerTyrPheTyrGly | 628 |
| 1975 | AAAATATTAATTTTGCATGAAGGTAGCAGCTATTTTTATGGG | 2016 |
| 629 | ThrPheSerGluLeuGlnAsnLeuGlnProAspPheSerSer | 642 |
| 2017 | ACATTTTCAGAACTCCAAAATCTACAGCCAGACTTTAGCTCA | 2058 |

FIG. 14C

| | | |
|---|---|---|
| 643 | LysLeuMetGlyCysAspSerPheAspGlnPheSerAlaGlu | 656 |
| 2059 | AAACTCATGGGATGTGATTCTTTCGACCAATTTAGTGCAGAA | 2100 |
| 657 | ArgArgAsnSerIleLeuThrGluThrLeuHisArgPheSer | 670 |
| 2101 | AGAAGAAATTCAATCCTAACTGAGACCTTACACCGTTTCTCA | 2142 |
| 671 | LeuGluGlyAspAlaProValSerTrpThrGluThrLysLys | 684 |
| 2143 | TTAGAAGGAGATGCTCCTGTCTCCTGGACAGAAACAAAAAAA | 2184 |
| 685 | GlnSerPheLysGlnThrGlyGluPheGlyGluLysArgLys | 698 |
| 2185 | CAATCTTTTAAACAGACTGGAGAGTTTGGGGAAAAAAGGAAG | 2226 |
| 699 | AsnSerIleLeuAsnProIleAsnSerIleArgLysPheSer | 712 |
| 2227 | AATTCTATTCTCAATCCAATCAACTCTATACGAAAATTTTCC | 2268 |
| 713 | IleValGlnLysThrProLeuGlnMetAsnGlyIleGluGlu | 726 |
| 2269 | ATTGTGCAAAAGACTCCCTTACAAATGAATGGCATCGAAGAG | 2310 |
| 727 | AspSerAspGluProLeuGluArgArgLeuSerLeuValPro | 740 |
| 2311 | GATTCTGATGAGCCTTTAGAGAGAAGGCTGTCCTTAGTACCA | 2352 |
| 741 | AspSerGluGlnGlyGluAlaIleLeuProArgIleSerVal | 754 |
| 2353 | GATTCTGAGCAGGGAGAGGCGATACTGCCTCGCATCAGCGTG | 2394 |
| 755 | IleSerThrGlyProThrLeuGlnAlaArgArgArgGlnSer | 768 |
| 2395 | ATCAGCACTGGCCCCACGCTTCAGGCACGAAGGAGGCAGTCT | 2436 |
| 769 | ValLeuAsnLeuMetThrHisSerValAsnGlnGlyGlnAsn | 782 |
| 2437 | GTCCTGAACCTGATGACACACTCAGTTAACCAAGGTCAGAAC | 2478 |
| 783 | IleHisArgLysThrThrAlaSerThrArgLysValSerLeu | 796 |
| 2479 | ATTCACCGAAAGACAACAGCATCCACACGAAAAGTGTCACTG | 2520 |
| 797 | AlaProGlnAlaAsnLeuThrGluLeuAspIleTyrSerArg | 810 |
| 2521 | GCCCCTCAGGCAAACTTGACTGAACTGGATATATATTCAAGA | 2562 |
| 811 | ArgLeuSerGlnGluThrGlyLeuGluIleSerGluGluIle | 824 |
| 2563 | AGGTTATCTCAAGAAACTGGCTTGGAAATAAGTGAAGAAATT | 2604 |
| 825 | AsnGluGluAspLeuLysGluCysLeuPheAspAspMetGlu | 838 |
| 2605 | AACGAAGAAGACTTAAAGGAGTGCCTTTTTGATGATATGGAG | 2646 |
| 839 | SerIleProAlaValThrThrTrpAsnThrTyrLeuArgTyr | 852 |
| 2647 | AGCATACCAGCAGTGACTACATGGAACACATACCTTCGATAT | 2688 |
| 853 | IleThrValHisLysSerLeuIlePheValLeuIleTrpCys | 866 |
| 2689 | ATTACTGTCCACAAGAGCTTAATTTTTGTGCTAATTTGGTGC | 2730 |

FIG. 14D

| | | |
|---|---|---|
| 867 | LeuValIlePheLeuAlaGluValAlaAlaSerLeuValVal | 880 |
| 2731 | TTAGTAATTTTTCTGGCAGAGGTGGCTGCTTCTTTGGTTGTG | 2772 |
| 881 | LeuTrpLeuLeuGlyAsnThrProLeuGlnAspLysGlyAsn | 894 |
| 2773 | CTGTGGCTCCTTGGAAACACTCCTCTTCAAGACAAAGGGAAT | 2814 |
| 895 | SerThrHisSerArgAsnAsnSerTyrAlaValIleIleThr | 908 |
| 2815 | AGTACTCATAGTAGAAATAACAGCTATGCAGTGATTATCACC | 2856 |
| 909 | SerThrSerSerTyrTyrValPheTyrIleTyrValGlyVal | 922 |
| 2857 | AGCACCAGTTCGTATTATGTGTTTTACATTTACGTGGGAGTA | 2898 |
| 923 | AlaAspThrLeuLeuAlaMetGlyPhePheArgGlyLeuPro | 936 |
| 2899 | GCCGACACTTTGCTTGCTATGGGATTCTTCAGAGGTCTACCA | 2940 |
| 937 | LeuValHisThrLeuIleThrValSerLysIleLeuHisHis | 950 |
| 2941 | CTGGTGCATACTCTAATCACAGTGTCGAAAATTTTACACCAC | 2982 |
| 951 | LysMetLeuHisSerValLeuGlnAlaProMetSerThrLeu | 964 |
| 2983 | AAAATGTTACATTCTGTTCTTCAAGCACCTATGTCAACCCTC | 3024 |
| 965 | AsnThrLeuLysAlaGlyGlyIleLeuAsnArgPheSerLys | 978 |
| 3025 | AACACGTTGAAAGCAGGTGGGATTCTTAATAGATTCTCCAAA | 3066 |
| 979 | AspIleAlaIleLeuAspAspLeuLeuProLeuThrIlePhe | 992 |
| 3067 | GATATAGCAATTTTGGATGACCTTCTGCCTCTTACCATATTT | 3108 |
| 993 | AspPheIleGlnLeuLeuLeuIleValIleGlyAlaIleAla | 1006 |
| 3109 | GACTTCATCCAGTTGTTATTAATTGTGATTGGAGCTATAGCA | 3150 |
| 1007 | ValValAlaValLeuGlnProTyrIlePheValAlaThrVal | 1020 |
| 3151 | GTTGTCGCAGTTTTACAACCCTACATCTTTGTTGCAACAGTG | 3192 |
| 1021 | ProValIleValAlaPheIleMetLeuArgAlaTyrPheLeu | 1034 |
| 3193 | CCAGTGATAGTGGCTTTTATTATGTTGAGAGCATATTTCCTC | 3234 |
| 1035 | GlnThrSerGlnGlnLeuLysGlnLeuGluSerGluGlyArg | 1048 |
| 3235 | CAAACCTCACAGCAACTCAAACAACTGGAATCTGAAGGCAGG | 3276 |
| 1049 | SerProIlePheThrHisLeuValThrSerLeuLysGlyLeu | 1062 |
| 3277 | AGTCCAATTTTCACTCATCTTGTTACAAGCTTAAAAGGACTA | 3318 |
| 1063 | TrpThrLeuArgAlaPheGlyArgGlnProTyrPheGluThr | 1076 |
| 3319 | TGGACACTTCGTGCCTTCGGACGGCAGCCTTACTTTGAAACT | 3360 |
| 1077 | LeuPheHisLysAlaLeuAsnLeuHisThrAlaAsnTrpPhe | 1090 |
| 3361 | CTGTTCCACAAAGCTCTGAATTTACATACTGCCAACTGGTTC | 3402 |

FIG. 14E

| | | |
|---|---|---|
| 1091 | LeuTyrLeuSerThrLeuArgTrpPheGlnMetArgIleGlu | 1104 |
| 3403 | TTGTACCTGTCAACACTGCGCTGGTTCCAAATGAGAATAGAA | 3444 |
| 1105 | MetIlePheValIlePhePheIleAlaValThrPheIleSer | 1118 |
| 3445 | ATGATTTTTGTCATCTTCTTCATTGCTGTTACCTTCATTTCC | 3486 |
| 1119 | IleLeuThrThrGlyGluGlyGluGlyArgValGlyIleIle | 1132 |
| 3487 | ATTTTAACAACAGGAGAAGGAGAAGGAAGAGTTGGTATTATC | 3528 |
| 1133 | LeuThrLeuAlaMetAsnIleMetSerThrLeuGlnTrpAla | 1146 |
| 3529 | CTGACTTTAGCCATGAATATCATGAGTACATTGCAGTGGGCT | 3570 |
| 1147 | ValAsnSerSerIleAspValAspSerLeuMetArgSerVal | 1160 |
| 3571 | GTAAACTCCAGCATAGATGTGGATAGCTTGATGCGATCTGTG | 3612 |
| 1161 | SerArgValPheLysPheIleAspMetProThrGluGlyLys | 1174 |
| 3613 | AGCCGAGTCTTTAAGTTCATTGACATGCCAACAGAAGGTAAA | 3654 |
| 1175 | ProThrLysSerThrLysProTyrLysAsnGlyGlnLeuSer | 1188 |
| 3655 | CCTACCAAGTCAACCAAACCATACAAGAATGGCCAACTCTCG | 3696 |
| 1189 | LysValMetIleIleGluAsnSerHisValLysLysAspAsp | 1202 |
| 3697 | AAAGTTATGATTATTGAGAATTCACACGTGAAGAAAGATGAC | 3738 |
| 1203 | IleTrpProSerGlyGlyGlnMetThrValLysAspLeuThr | 1216 |
| 3739 | ATCTGGCCCTCAGGGGGCCAAATGACTGTCAAAGATCTCACA | 3780 |
| 1217 | AlaLysTyrThrGluGlyGlyAsnAlaIleLeuGluAsnIle | 1230 |
| 3781 | GCAAAATACACAGAAGGTGGAAATGCCATATTAGAGAACATT | 3822 |
| 1231 | SerPheSerIleSerProGlyGlnArgValGlyLeuLeuGly | 1244 |
| 3823 | TCCTTCTCAATAAGTCCTGGCCAGAGGGTGGGCCTCTTGGGA | 3864 |
| 1245 | ArgThrGlySerGlyLysSerThrLeuLeuSerAlaPheLeu | 1258 |
| 3865 | AGAACTGGATCAGGGAAGAGTACTTTGTTATCAGCTTTTTTG | 3906 |
| 1259 | ArgLeuLeuAsnThrGluGlyGluIleGlnIleAspGlyVal | 1272 |
| 3907 | AGACTACTGAACACTGAAGGAGAAATCCAGATCGATGGTGTG | 3948 |
| 1273 | SerTrpAspSerIleThrLeuGlnGlnTrpArgLysAlaPhe | 1286 |
| 3949 | TCTTGGGATTCAATAACTTTGCAACAGTGGAGGAAAGCCTTT | 3990 |
| 1287 | GlyValIleProGlnLysValPheIlePheSerGlyThrPhe | 1300 |
| 3991 | GGAGTGATACCACAGAAAGTATTTATTTTTTCTGGAACATTT | 4032 |
| 1301 | ArgLysAsnLeuAspProTyrGluGlnTrpSerAspGlnGlu | 1314 |
| 4033 | AGAAAAAACTTGGATCCCTATGAACAGTGGAGTGATCAAGAA | 4074 |

FIG. 14F

| | | |
|---|---|---|
| 1315 | IleTrpLysValAlaAspGluValGlyLeuArgSerValIle | 1328 |
| 4075 | ATATGGAAAGTTGCAGATGAGGTTGGGCTCAGATCTGTGATA | 4116 |
| | | |
| 1329 | GluGlnPheProGlyLysLeuAspPheValLeuValAspGly | 1342 |
| 4117 | GAACAGTTTCCTGGGAAGCTTGACTTTGTCCTTGTGGATGGG | 4158 |
| | | |
| 1343 | GlyCysValLeuSerHisGlyHisLysGlnLeuMetCysLeu | 1356 |
| 4159 | GGCTGTGTCCTAAGCCATGGCCACAAGCAGTTGATGTGCTTG | 4200 |
| | | |
| 1357 | AlaArgSerValLeuSerLysAlaLysIleLeuLeuLeuAsp | 1370 |
| 4201 | GCTAGATCTGTTCTCAGTAAGGCGAAGATCTTGCTGCTTGAT | 4242 |
| | | |
| 1371 | GluProSerAlaHisLeuAspProValThrTyrGlnIleIle | 1384 |
| 4243 | GAACCCAGTGCTCATTTGGATCCAGTAACATACCAAATAATT | 4284 |
| | | |
| 1385 | ArgArgThrLeuLysGlnAlaPheAlaAspCysThrValIle | 1398 |
| 4285 | AGAAGAACTCTAAAACAAGCATTTGCTGATTGCACAGTAATT | 4326 |
| | | |
| 1399 | LeuCysGluHisArgIleGluAlaMetLeuGluCysGlnGln | 1412 |
| 4327 | CTCTGTGAACACAGGATAGAAGCAATGCTGGAATGCCAACAA | 4368 |
| | | |
| 1413 | PheLeuValIleGluGluAsnLysValArgGlnTyrAspSer | 1426 |
| 4369 | TTTTTGGTCATAGAAGAGAACAAAGTGCGGCAGTACGATTCC | 4410 |
| | | |
| 1427 | IleGlnLysLeuLeuAsnGluArgSerLeuPheArgGlnAla | 1440 |
| 4411 | ATCCAGAAACTGCTGAACGAGAGGAGCCTCTTCCGGCAAGCC | 4452 |
| | | |
| 1441 | IleSerProSerAspArgValLysLeuPheProHisArgAsn | 1454 |
| 4453 | ATCAGCCCCTCCGACAGGGTGAAGCTCTTTCCCCACCGGAAC | 4494 |
| | | |
| 1455 | SerSerLysCysLysSerLysProGlnIleAlaAlaLeuLys | 1468 |
| 4495 | TCAAGCAAGTGCAAGTCTAAGCCCCAGATTGCTGCTCTGAAA | 4536 |
| | | |
| 1469 | GluGluThrGluGluGluValGlnAspThrArgLeuEnd | 1482 |
| 4537 | GAGGAGACAGAAGAAGAGGTGCAAGATACAAGGCTTTAGAGA | 4578 |
| 4579 | GCAGCATAAATGTTGACATGGACATTTGCTCATGGAATTGG | 4620 |
| 4621 | AGCTCGTGGGACAGTCACCTCATGGAATTGGAGCTCGTGGAA | 4662 |
| 4663 | CAGTTACCTCTGCCTCAGAAAACAAGGATGAATTAAGTTTTT | 4704 |
| 4705 | TTTTAAAAAAGAAACATTTGGTAAGGGAATTGAGGACACTG | 4746 |
| 4747 | ATATGGGTCTTGATAAATGGCTTCCTGGCAATAGTCAAATTG | 4788 |
| 4789 | TGTGAAAGGTACTTCAAATCCTTGAAGATTTACCACTTGTGT | 4830 |
| 4831 | TTTGCAAGCCAGATTTTCCTGAAAACCCTTGCCATGTGCTAG | 4872 |
| 4873 | TAATTGGAAAGGCAGCTCTAAA | 4894 |

FIG. 14G

METHOD FOR PRODUCING DNA ENCODING CYSTIC FIBROSIS TRANSMEMBRANE CONDUCTANCE REGULATOR (CFTR) PROTEIN IN *E. COLI*

RELATED APPLICATIONS

This application is a continuation of U.S. application Ser. No. 08/087,132, filed on Jul. 2, 1993, itself a continuation of Ser. No. 07/613,592 filed on Nov. 15, 1990 and now abandoned, itself a continuation-in-part of Ser. No. 07/589,295 filed on Sep. 27, 1990 and now abandoned, itself a continuation-in-part of Ser. No. 07/488,307 itself filed Mar. 5, 1990 and also now abandoned. The disclosure (including all of the text, figures, tables, sequences and claims thereof) of the aforementioned Ser. No. 08/087,132 application is fully incorporated herein by reference. The disclosures of the other aforementioned parent applications are incorporated herein by reference also, to the extent permitted by law.

To the extent permitted by law there is also incorporated by reference herein any and all disclosure from the parent applications of the present application that may presently be found in any of the following copending members of the patent family hereof, 07/935,603; 08/072,708; 08/112,592; 08/135,809; 08/114,950; 08/117,954; 08/118,054; 08/136,742 and 08/130,682.

FIELD OF THE INVENTION

This invention relates to the use of recombinant DNA techniques to produce the cystic fibrosis transmembrane conductance regulator (CFTR), and in particular it relates to new methods for detecting CFTR and CFTR related defects and to new treatment methods therefor. Viral vectors, and vectors containing viral elements, that comprise DNA sequences encoding CFTR are also disclosed.

BACKGROUND OF THE INVENTION

Cystic fibrosis (CF) is the most common fatal genetic disease in humans (Boat et al., 1989). Based on both genetic and molecular analysis, a gene associated with CF was recently isolated as part of 21 individual cDNA clones and its protein product predicted (Kerem et al., 1989; Riordan et al., 1989; Rommens et al., 1989). U.S. Ser. No. 488,307 describes the construction of the gene into a continuous strand and confirmed the gene is responsible for CF by introduction of a cDNA copy of the coding sequence into epithelial cells from CF patients (See also Gregory et al., 1990; Rich et al., 1990). Wild type but not a mutant version of the cDNA complemented the defect in the cAMP regulated chloride channel shown previously to be characteristic of CF. Similar conclusions were reported by others (Drumm et al., 1990).

The protein product of the CF associated gene is called the cystic fibrosis transmembrane conductance regulator (CFTR) (Riordan et al., 1989). CFTR is a protein of approximately 1480 amino acids made up of two repeated elements, each comprising six transmembrane segments and a nucleotide binding domain. The two repeats are separated by a large, polar, so-called R-domain containing multiple potential phosphorylation sites. Based on its predicted domain structure, CFTR is a member of a class of related proteins which includes the multi-drug resistance (MDR) or P-glycoprotein, bovine adenyl cyclase, the yeast STE6 protein as well as several bacterial amino acid transport proteins (Riordan et al., 1989; Hyde et al., 1990). Proteins in this group, characteristically, are involved in pumping molecules into or out of cells.

CFTR is a large, multi domain, integral membrane protein which is postulated to regulate the outward flow of anions from epithelial cells in response to phosphorylation by cyclic AMP-dependant protein kinase or protein kinase C (Riordan et al., 1989; Welsh,1986; Frizzel etal., 1986; Welsh and Liedtke, 1986; Schoumacher et al., 1987; Li et al., 1988; Hwang et al., 1989; Li et al., 1989).

To investigate the function of the CFTR, the mechanism by which mutations in the CFTR gene cause cystic fibrosis, to develop potential therapies for cystic fibrosis, and for many other applications, a cDNA clone encoding the entire CFTR protein is necessary.

It is an aspect of the present invention to engineer CFTR cDNA sequences containing all of the coding information for CFTR protein on a single recombinant DNA molecule which can be stably propagated in *E. coli* and transferred to yeast, insect, plant or mammalian cells, or transgenic animals, for expression of wild-type CFTR protein, as well as mutants to provide derivatives which correlate with the cystic fibrosis disease.

It is another aspect to provide the critical cDNA gene containing the correct gene sequence in order to provide for production of the CFTR protein.

It is yet another aspect to enable various diagnostic, therapeutic and protein production techniques related to the evaluation and treatment of cystic fibrosis caused by faulty CFTR function, faulty CFTR processing or related to the intracellular location of CFTR.

In addition, a mutation within the gene sequence encoding CFTR protein has been identified in DNA samples from patients with cystic fibrosis, the most common genetic disease of caucasians (Kerem et al., 1989). The mutation, which results in the deletion of the amino acid phenylalanine at position 508 of the CFTR amino acid sequence, is associated with approximately 70% of the cases of cystic fibrosis.

This mutation in the CFTR gene results in the failure of an epithelial cell chloride channel to respond to cAMP (Frizzell et al., 1986; Welsh, 1986; Li et al., 1988; Quinton, 1989). In airway cells, this leads to an imbalance in ion and fluid transport. It is widely believed that this causes abnormal mucus secretion, and ultimately results in pulmonary infection and epithelial cell damage. That the chloride channel can be regulated by cAMP in isolated membrane patches (Li et al., 1988) suggests that at least some CFTR is present in the apical plasma membrane and that CFTR responds to protein kinase A. Whether CFTR itself is a regulator of the membrane chloride channel or constitutes the channel itself remains controversial.

U.S. Ser. No. 488,307, fully incorporated herein, showed that CFTR is a membrane-associated glycoprotein that can be phosphorylated in vitro (Gregory et al., 1990). The protein has a primary translation product which migrates with apparent molecular weight on SDS-polyacrylamide gels of 130k (referred to as band A). In vaccinia virus-infected, cDNA transfected HeLa cells or in reticulocyte lysates containing canine pancreatic membranes, band A is modified by glycosylation to yield a version of apparent molecular weight 135 kd called band B. The use of polyclonal and monoclonal antibodies to CFTR showed that non-recombinant T84 cells contain, in addition, a diffusely migrating 150 kd (band C) version of CFTR.

It is another aspect of the present invention to study structure:function relationships in CFTR by constructing a site specific mutation which provides for the deletion of phenylalanine 508 (referred to as ΔF508).

It is yet another aspect to characterize variant CFTR protein forms associated with a number of less frequent CF associated mutations, as well as mutations in residues predicted to play an important role in the function of CFTR.

It is still yet another aspect of the present invention to more fully describe the characteristics of CFTR associated with bands a, b and c.

It is yet still another aspect of the present invention to provide new diagnostic and therapeutic methods for CF which rely upon intracellular processing mechanism for CFTR and intracellular location of variously processed CFTR.

SUMMARY OF THE INVENTION

In accordance with the principles and aspects of the present invention there are provided recombinant DNA molecules encoding CFTR including most preferred cDNA molecules which can be stably propagated in host *E. coli* cells and which can be used to transform mammalian cells resulting in expression of CFTR. These DNA molecules are ideally maintained at low gene dosage in the host, thereby reducing the potential toxicity caused by inadvertent or inappropriate expression of the CFTR cDNA. In addition, there are provided recombinant cDNA molecules containing at least one intervening sequence within the CFTR coding sequence. Such a sequence advantageously disrupts expression of protein from the CFTR cDNA in *E. coli* cells, but allows expression in mammalian cells since such cells are capable of removing the intervening sequence from the initial CFTR RNA transcript. Also included are DNA sequences encoding CFTR but containing one or more point mutations.

Preferred embodiments of the present invention include cDNA's coding for the entire CFTR protein coding sequence of 4440 nucleotides and advantageously include regulatory sequences from the flanking regions of the cDNA, such as the ribosome binding site located immediately upstream of the initiator methionine of the CFTR open reading frame (Kozak, 1984, Kozak, 1986). These cDNA's are ideally cloned in plasmid vectors containing origins of replication that allow maintenance of recombinant plasmids at low copy number in *E. coli* cells. These origins of replication may be advantageously selected from those for the *E. coli* plasmids pMB1 (15–20 copies per cell), p15A (10–12 copies per cell) or pSC101 (approximately 5 copies per cell) or other vectors which are maintained at low copy number (e.g. less than about 25) in *E. coli* cells (Sambrook et al., 1989).

Also described herein are CFTR cDNAs containing a synthetic intron of 83 base pairs between nucleotide positions 1716 and 1717 of the CFTR cDNA sequence, which acts to stabilize the cDNA by disrupting the translational reading frame of the CFTR protein such that neither full length protein nor extensive polypeptide sequences can be synthesized in cells unable to splice mRNA. This allows replication in (but not CFTR expression) prokaryotic cells of the CFTR cDNA for subsequent transformation of eukaryotic host cells, most preferably mammalian cells, for subsequent CFTR expression. Additional embodiments of the invention include full length mutant CFTR cDNAs which encode a protein from which amino-acid 508 has been deleted. Still other preferred embodiments include expression vectors for expression of said CFTR cDNA's in bacterial, yeast, plant, insect and mammalian cells, and transgenic animals the CFTR proteins derived from these expression systems, pharmaceutical compositions comprising such recombinantly produced CFTR proteins as well as associated diagnostic and therapeutic methods.

A most preferred embodiment includes mature CFTR protein, discovered to be associated with band c (described in detail below), having an apparent molecular weight of approximately 150 kd and modified by complex-type N-linked glycosylation at residues 894 and/or 900. It has been unexpectedly discovered that mature CFTR is lacking from recombinant cells encoding several mutant versions of the protein. Also described are new diagnostic assays for detecting individuals suffering from cystic fibrosis as well as therapeutic methods for treating such individuals based, in part, upon the mechanism of intracellular processing of CFTR discovered in the present invention.

This invention also provides for viral vectors (and vectors containing viral elements) comprising DNA sequences encoding CFTR.

BRIEF DESCRIPTION OF THE TABLE AND DRAWINGS

Further understanding of the invention may be had by reference to the tables and figures wherein:

Table 1 shows CFTR mutants wherein the known association with CF (Y, yes or N, no), exon localization, domain location and presence (+) or absence (−) of bands A, B and C of mutant CFTR species is shown. TM6, indicates transmembrane domain 6; NBD nucleotide binding domain; ECD, extracellular domain and Term, termination at 21 codons past residue 1337.

The convention for naming mutants is first the amino acid normally found at the particular residue, the residue number (Riordan et al., 1989) and the amino acid to which the residue was converted. The single letter amino acid code is used: D, aspartic acid; F, phenylalanine; G, glycine; I, isoleucine; K, lysine; M, methionine; N, asparagine; Q, glutamine; R, arginine; S, serine; W, tryptophan. Thus G551D is a mutant in which glycine 551 is converted to aspartic acid;

FIGS. 14A–14G show the sequence of that portion of CFTR cDNA encoding the complete CFTR protein within plasmid pSC-CFTR2 including the amino acid sequence of the CFTR open reading frame.

DETAILED DESCRIPTION AND BEST MODE

Definitions

Figure 1:
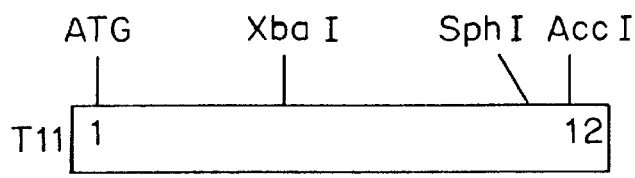
FIG. 1 shows alignment of CFTR partial cDNA clones used in construction of cDNA containing complete coding sequence of the CFTR, only restriction sites relevant to the DNA constructions described below are shown.
Figure 1:
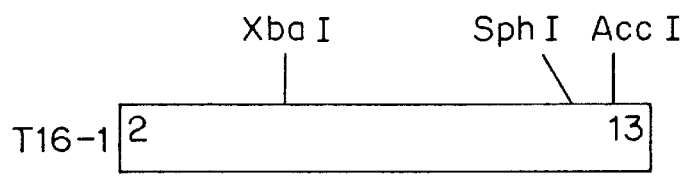
Figure 1:
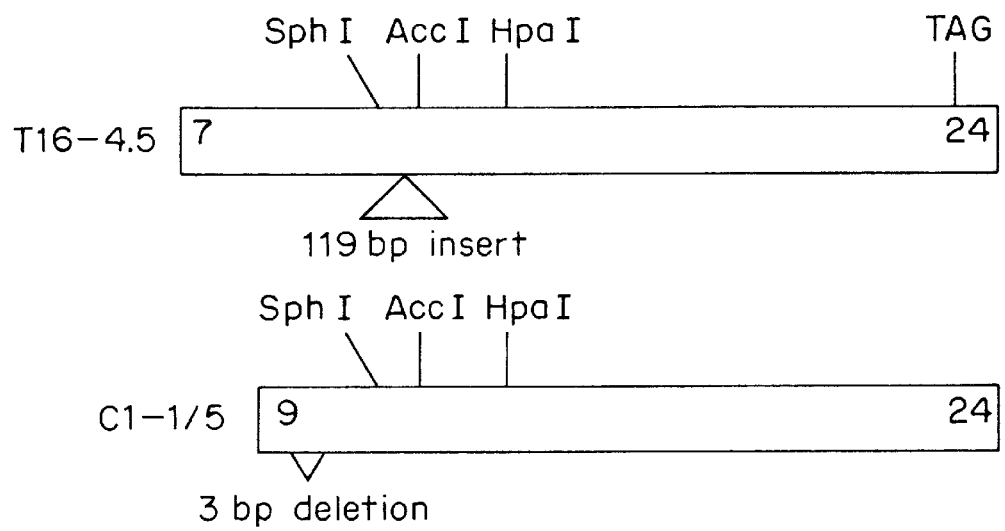

The term "intron" identifies an intervening sequence within a gene for the gene product that does not constitute protein coding sequences. In eukaryotic cells introns are removed from the primary RNA transcript to produce the mature mRNA.

The term "splice" refers to the removal of an intron from the primary RNA transcript of a gene.

The term "polylinker" refers a closely arranged series of synthetic restriction enzyme cleavage sites within a plasmid.

The term "open reading frame" refers to a nucleotide sequence with the potential for encoding a protein.

The term "agarose gel purification" refers to the separation of DNA restriction fragments by electrophoresis through an agarose gel followed by purification of the desired DNA fragments from the agarose gel as described below in general methods.

The term "maintained" refers to the stable presence of a plasmid within a transformed host cell wherein the plasmid is present as an autonomously replicating body or as an integrated portion of the host's genome.

The term "cell culture" refers to the containment of growing cells derived from either a multicellular plant or animal which allows the cells to remain viable outside of the original plant or animal.

The term "host cell" refers to a microorganism including yeast, bacteria, insect and mammalian cells which can be grown in cell culture and transfected or transformed with a plasmid or vector encoding a molecule having a CFTR biological characteristic.

The terms "plasmid" and "vector" refer to an autonomous self-replicating extra-chromosomal circular DNA and includes both the expression and non-expression types. When a recombinant microorganism or cell culture providing expression of a molecule is described as hosting an expression plasmid, the term "expression plasmid" includes both extrachromosomal circular DNA and DNA that has been incorporated into the host chromosome(s).

The term "promoter" is a region of DNA involved in binding RNA polymerase to initiate transcription.

The term "DNA sequence" refers to a single- or double-stranded DNA molecule comprised of nucleotide bases, adenosine (A), thymidine (T), cytosine (C) and guanosine (G) and further includes genomic and complementary DNA (cDNA).

The term "ligate" refers to the joining of DNA fragments via a covalent phosphodiester bond, whose formation is catalyzed for example, by the enzyme T4 DNA ligase.

The term "upstream" identifies sequences proceeding in the opposite direction from expression; for example, the bacterial promoter is upstream from the transcription unit.

The term "restriction endonuclease", alternately referred to herein as a restriction enzyme, refers to one of a class of enzymes which cleave double-stranded DNA (dsDNA) at locations or sites characteristic to the particular enzyme. For example the restriction endonuclease Eco RI cleaves dsDNA only at locations:

| 5'GAATTC3' | to form | 5'G | and | AATTC3' | fragments |
| 3'CTTAAG5' | | 3'CTTAA | | G5' | |

Although many such enzymes are known, the most preferred embodiments of the present invention are primarily concerned with only selected restriction enzymes having specified characteristics.

All cited references are fully incorporated herein by reference, subsequent citations of previously cited references shall be by author only. Referenced citations, if not within the body of the text, may be found at the end hereof.

Within illustrations of plasmid constructions, only restriction endonuclease cleavage sites relevant to the particular construction being depicted are shown. Numbering of nucleotides and amino acids correspond to the published CFTR cDNA sequence of Riordan et al., compiled from partial CFTR cDNA clones.

General Methods

Methods of DNA preparation, restriction enzyme cleavage, restriction enzyme analysis, gel electrophoresis, DNA precipitation, DNA fragment ligation, bacterial transformation, bacterial colony selection and growth are as detailed in Sambrook et al. DNA fragment isolation from agarose gels was performed by crushing the agarose gel slice containing the fragment of interest in 300 microliters of phenol, freezing the phenol/gel slice mixture at −70° C. for 5 minutes, centrifuging and separating the aqueous phase from the phenol and extracting the aqueous phase with chloroform. The DNA fragments were recovered from the aqueous phase by ethanol precipitation. Methods of in vitro transcription in a buffered medium and in vitro protein translation in rabbit reticulocyte lysates were employed as detailed in the manufacturers instructions (Strategene and Promega respectively). DNA sequencing was performed using the Sanger dideoxy method using denatured double-stranded DNA (Sanger et al., Proc. Natl. Acad. Sci. 74, 5463 (1977)).

CFTR Partial cDNA Source

Partial CFTR cDNA clones T11, T16-1, T16-4.5 and C1-1/5 (Riordan et al.) were obtained from the American Type Culture Collection (Rockland, Md.). A linear alignment of the CFTR cDNA portion of these clones is presented in FIG. 1. Exons at the end of the individual cDNA clones are indicated by the numbers 1, 2, 7, 9, 12, 13 and 24. Also indicated are the initiation codon of the CFTR protein coding sequence (ATG), the termination codon (TAG), as well as restriction endonuclease sites within the CFTR cDNA which were used in subsequent DNA manipulations.

EXAMPLE 1

Generation of Full Length CFTR cDNAs

Initial attempts to reconstruct the entire CFTR protein coding sequence in high copy number plasmids similar to those reported by Riordan et al., produced only molecules with internal rearrangements and deletions of coding sequence. Such rearrangements can result, for example, from recombination catalyzed by host cell proteins, and they occur primarily between regions of complete or partial nucleotide sequence identity within a DNA molecule, such as are present at direct or inverted repeat sequences. Although such deletions could be attributed to instability of the CFTR cDNA in E. coli, computer analysis of the CFTR sequence did not reveal an unusual number of direct and inverted sequence repeats within the published CFTR sequence, thereby indicating that the CFTR cDNA should not be inherently unstable in E. coli.

Nearly all of the commonly used DNA cloning vectors are based on plasmids containing modified pMB1 replication origins and are present at up to 500 to 700 copies per cell (Sambrook et al.). The partial CFTR cDNA clones isolated by Riordan et al. were maintained in such a plasmid. We postulated that an alternative theory to intrinsic clone instability to explain the apparent inability to recover clones encoding full length CFTR protein using high copy number plasmids, was that it was not possible to clone large segments of the CFTR cDNA at high gene dosage in E. coli. Expression of the CFTR or portions of the CFTR from regulatory sequences capable of directing transcription and/ or translation in the bacterial host cell might result in inviability of the host cell due to toxicity of the transcript or of the full length CFTR protein or fragments thereof. This inadvertent gene expression could occur from either plasmid regulatory sequences or cryptic regulatory sequences within the recombinant CFTR plasmid which are capable of functioning in E. coli. Toxic expression of the CFTR coding sequences would be greatly compounded if a large number of copies of the CFTR cDNA were present in cells because a high copy number plasmid was used. If the product was indeed toxic as postulated, the growth of cells containing full length and correct sequence would be actively disfavored. Based upon this novel hypothesis, the following procedures were undertaken.

Figure 2:
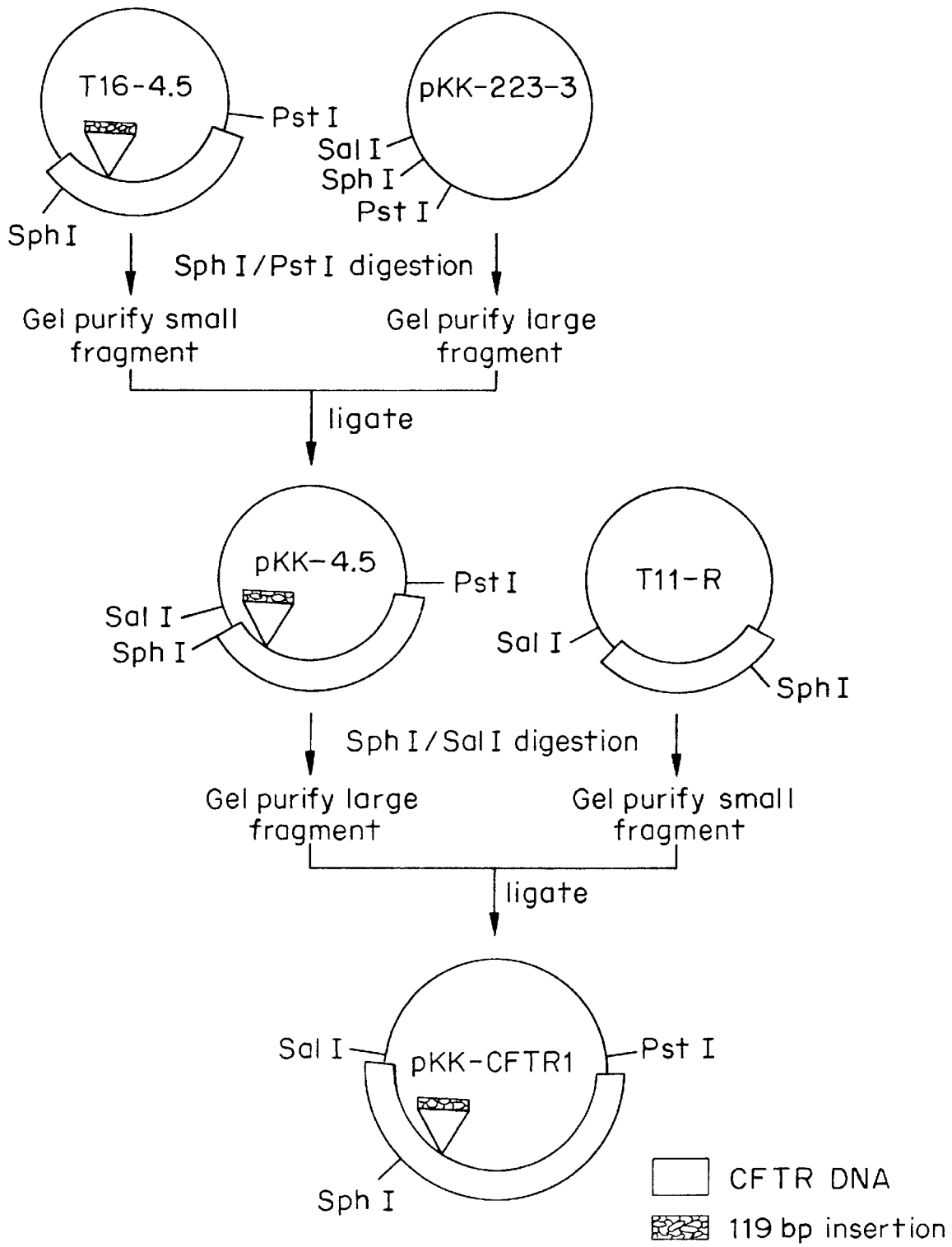
FIG. 2 depicts plasmid construction of the CFTR cDNA clone pKK-CFTR1.

With reference to FIG. 2, partial CFTR clone T16-4.5 was cleaved with restriction enzymes Sph I and Pst I and the resulting 3.9 kb restriction fragment containing exons 11 through most of exon 24 (including an uncharacterized 119 bp insertion reported by Riordan et al. between nucleotides 1716 and 1717), was isolated by agarose gel purification and ligated between the Sph I and Pst I sites of the pMB1 based vector pKK223-3 (Brosius and Holy, Proc. Natl. Acad. Sci. 81, 6929 (1984)). It was hoped that the pMB1 origin contained within this plasmid would allow it and plasmids constructed from it to replicate at 15–20 copies per host E. coli cell (Sambrook et al.). The resultant plasmid clone was called pKK-4.5.

Partial CFTR clone T11 was cleaved with Eco RI and Hinc II and the 1.9 kb band encoding the first 1786 nucleotides of the CFTR cDNA plus an additional 100 bp of DNA at the 5' end was isolated by agarose gel purification. This restriction fragment was inserted between the Eco RI site and Sma I restriction site of the plasmid pBluescript SK⁻ (Strategene, catalogue number 212206), such that the CFTR sequences were now flanked on the upstream (5') side by a Sal I site from the cloning vector. This clone, designated T11-R, was cleaved with Sal I and Sph I and the resultant 1.8 kb band isolated by agarose gel purification. Plasmid pKK-4.5 was cleaved with Sal I and Sph I and the large fragment was isolated by agarose gel purification. The purified T11-R fragment and pKK-4.5 fragments were ligated to construct pKK-CFTR1. pKK-CFTR1 contains exons 1 through 24 of the CFTR cDNA. It was discovered that this plasmid is stably maintained in E. coli cells and confers no measurably disadvantageous growth characteristics upon host cells.

pKK-CFTR1 contains, between nucleotides 1716 and 1717, the 119 bp insert DNA derived from partial cDNA clone T16-4.5 described above. In addition, subsequent sequence analysis of pKK-CFTR1 revealed unreported differences in the coding sequence between that portion of CFTR1 derived from partial cDNA clone T11 and the published CFTR cDNA sequence. These undesired differences included a 1 base-pair deletion at position 995 and a C to T transition at position 1507.

Figure 3:
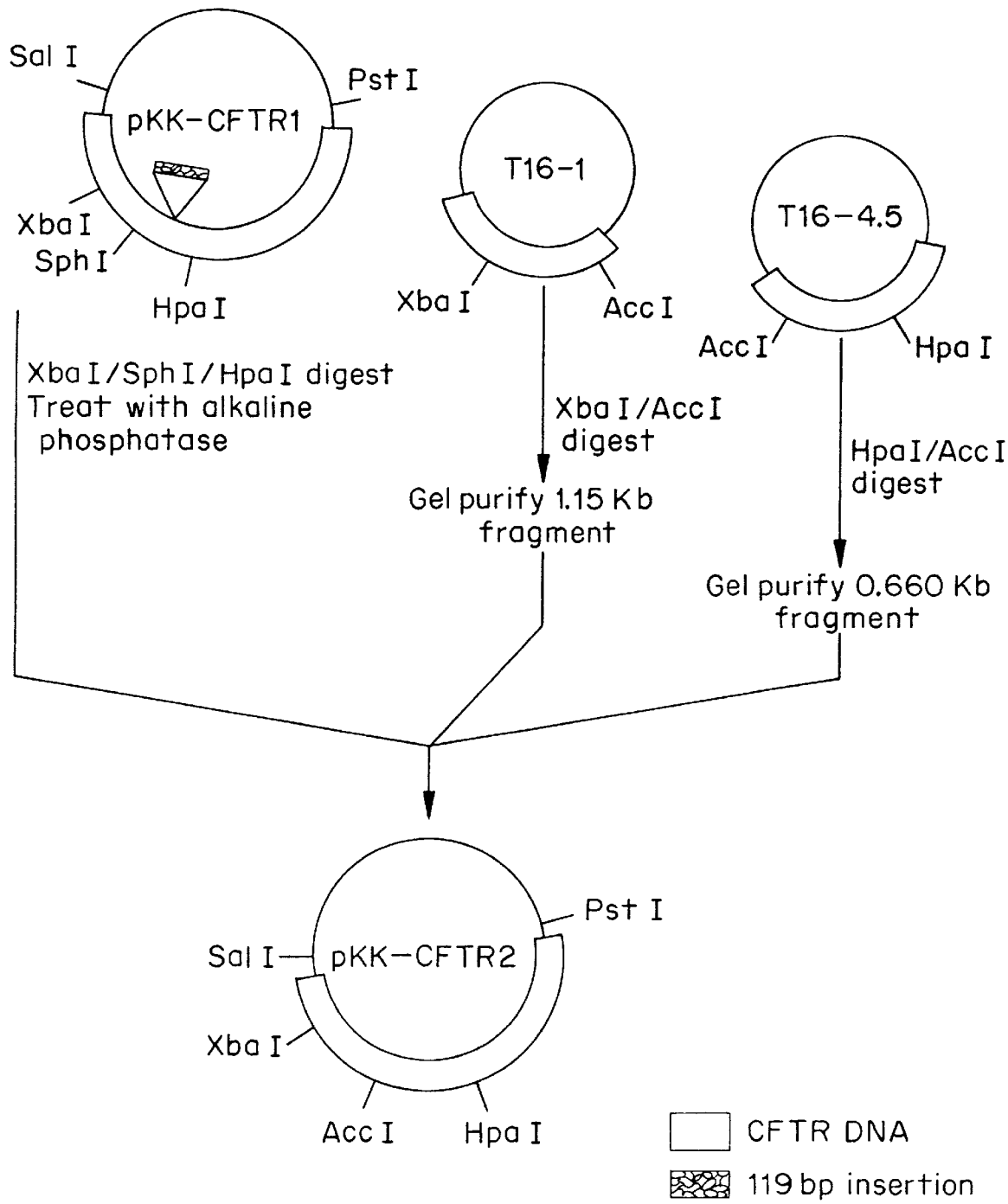
FIG. 3 depicts plasmid construction of the CFTR cDNA clone pKK-CFTR2.

To complete construction of an intact correct CFTR coding sequence without mutations or insertions and with reference to the construction scheme shown in FIG. 3, pKK-CFTR1 was cleaved with Xba I and Hpa I and dephosphorylated with calf intestinal alkaline phosphatase. In addition, to reduce the likelihood of recovering the original clone, the small unwanted Xba I/Hpa I restriction fragment from pKK-CFTR1 was digested with Sph I. T16-1 was cleaved with Xba I and Acc I and the 1.15 kb fragment isolated by agarose gel purification. T16-4.5 was cleaved with Acc I and Hpa I and the 0.65 kb band was also isolated by agarose gel purification. The two agarose gel purified restriction fragments and the dephosphorylated pKK-CFTR1 were ligated to produce pKK-CFTR2. Alternatively, pKK-CFTR2 could have been constructed using corresponding restriction fragments from the partial CFTR cDNA clone C1-⅕. pKK-CFTR2 contains the uninterrupted CFTR protein coding sequence and conferred slow growth upon E. coli host cells in which it was inserted, whereas pKK-CFTR1 did not. The origin of replication of pKK-CFTR2 is derived from pMB1 and confers a plasmid copy number of 15–20 copies per host cell.

EXAMPLE 2

Improving Host Cell Viability

An additional enhancement of host cell viability was accomplished by a further reduction in the copy number of CFTR cDNA per host cell. This was achieved by transferring the CFTR cDNA into the plasmid vector, pSC-3Z. pSC-3Z was constructed using the pSC101 replication origin of the low copy number plasmid pLG338 (Stoker et al., Gene 18, 335 (1982)) and the ampicillin resistance gene and polylinker of pGEM-3Z (available from Promega). pLG338 was cleaved with Sph I and Pvu II and the 2.8 kb fragment containing the replication origin isolated by agarose gel purification. pGEM-3Z was cleaved with Alw NI, the resultant restriction fragment ends treated with T4 DNA polymerase and deoxynucleotide triphosphates, cleaved with Sph I and the 1.9 kb band containing the ampicillin resistance gene and the polylinker was isolated by agarose gel purification. The pLG338 and pGEM-3Z fragments were ligated together to produce the low copy number cloning vector pSC-3Z. pSC-3Z and other plasmids containing pSC101 origins of replication are maintained at approximately five copies per cell (Sambrook et al.).

Figure 4:
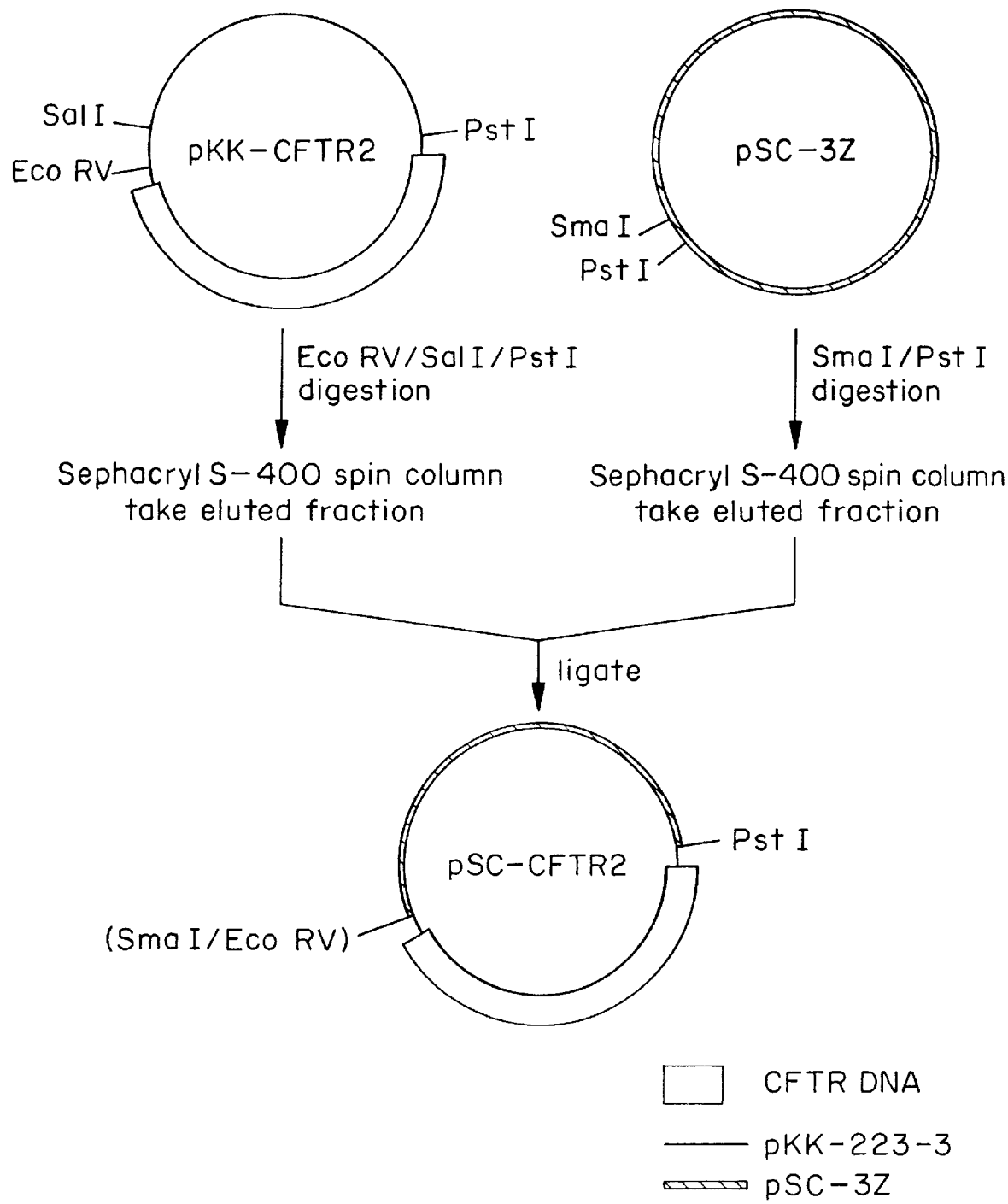
FIG. 4 depicts plasmid construction of the CFTR cDNA clone pSC-CFTR2.
Figure 5:
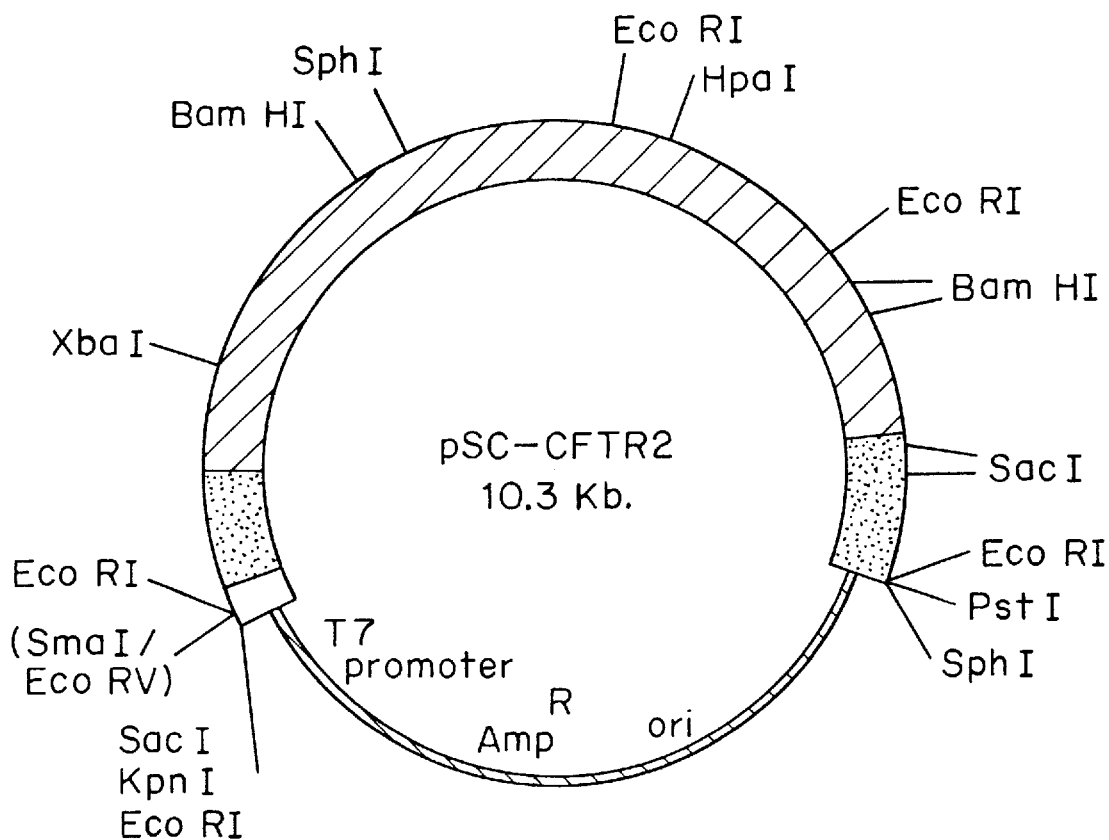
FIG. 5 shows a plasmid map of the CFTR cDNA clone pSC-CFTR2.

With additional reference to FIG. 4, pKK-CFTR2 was cleaved with Eco RV, Pst I and Sal I and then passed over a Sephacryl S400 spun column (available from Pharmacia) according to the manufacturer's procedure in order to remove the Sal I to Eco RV restriction fragment which was retained within the column. pSC-3Z was digested with Sma I and Pst I and also passed over a Sephacryl S400 spun column to remove the small Sma I/Pst I restriction fragment which was retained within the column. The column eluted fractions from the pKK-CFTR2 digest and the pSC-3Z digest were mixed and ligated to produce pSC-CFTR2. A map of this plasmid is presented in FIG. 5. Host cells containing CFTR cDNAs at this and similar gene dosages grow well and have stably maintained the recombinant plasmid with the full length CFTR coding sequence. In addition, this plasmid contains a bacteriophage T7 RNA polymerase promoter adjacent to the CFTR coding sequence and is therefore convenient for in vitro transcription/translation of the CFTR protein. The nucleotide sequence of CFTR coding region from pSC-CFTR2 plasmid is presented in FIG. 14. Significantly, this sequence differs from the previously published (Riordan et al.) CFTR sequence at position 1991, where there is C in place of the reported A. *E. coli* host cells containing pSC-CFTR2, internally identified with the number pSC-CFTR2/AG1, have been deposited at the American Type Culture Collection and given the accession number: ATCC 68244.

EXAMPLE 3

Alternate Method for Improving Host Cell Viability

Figure 6:
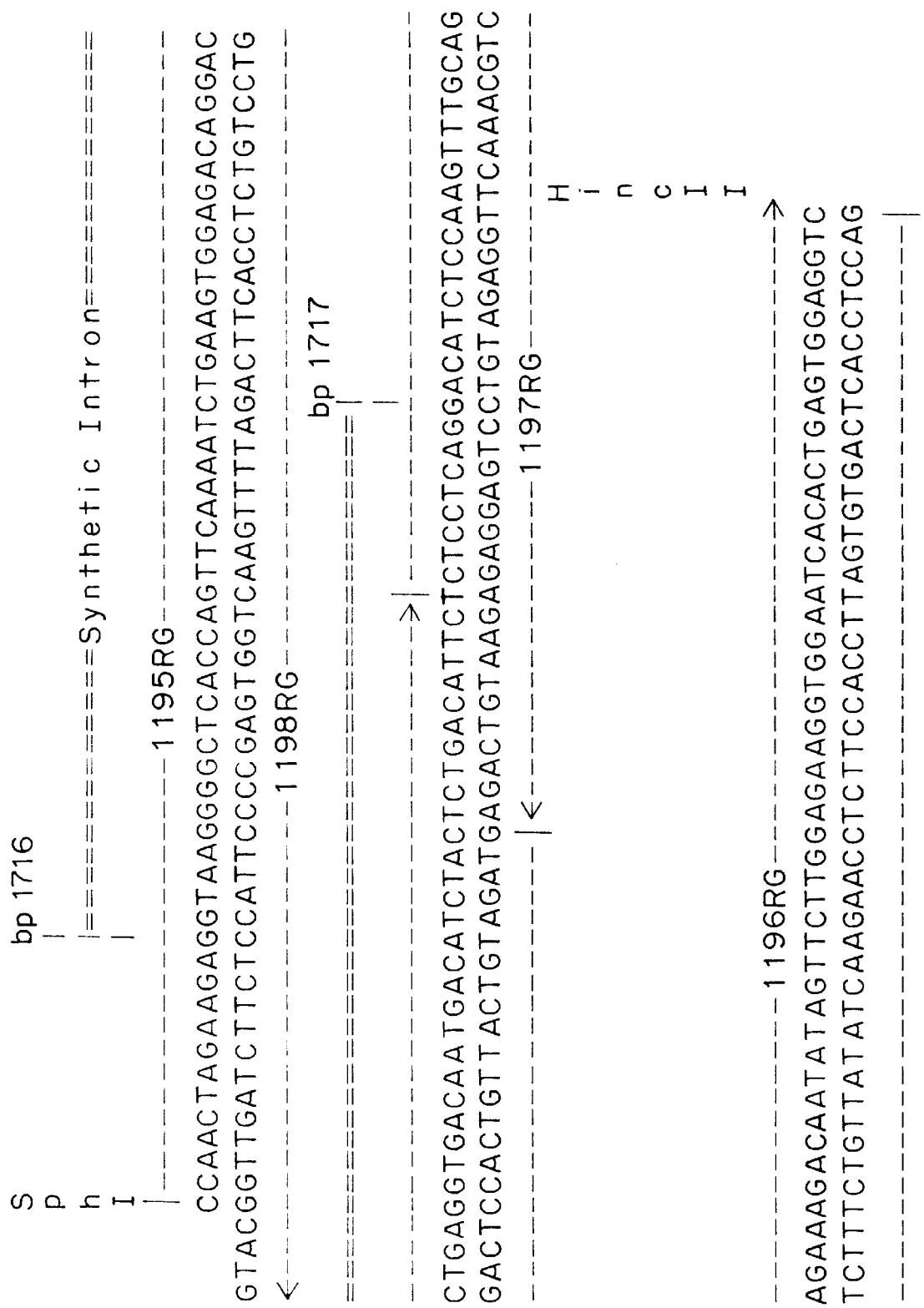
FIG. 6 shows the DNA sequence of synthetic DNAs used for insertion of an intron into the CFTR cDNA sequence, with the relevant restriction endonuclease sites and nucleotide positions noted.
Figure 7A:
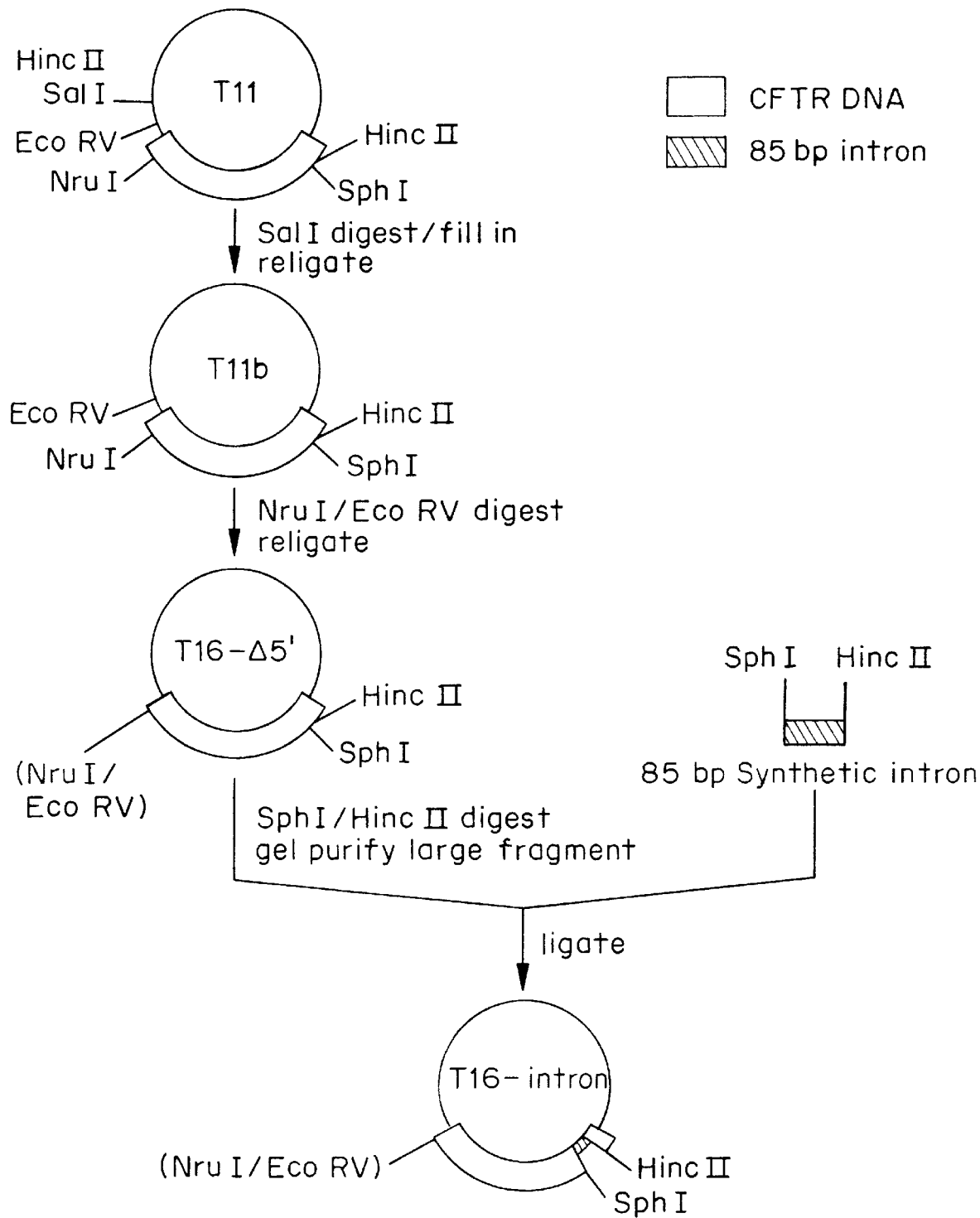
FIGS. 7A and 7B depict plasmid construction of the CFTR cDNA clone pKK-CFTR3.
Figure 7B:
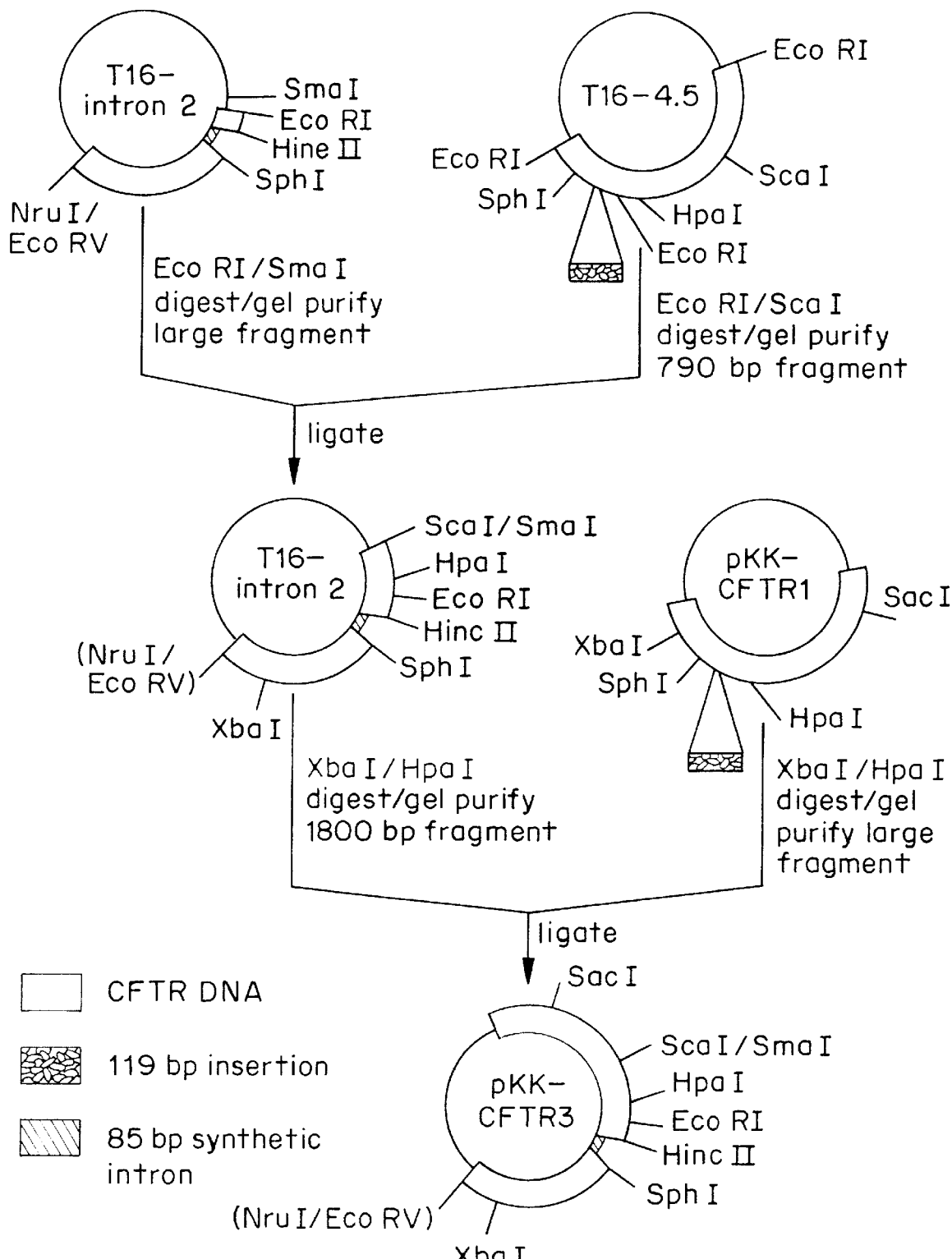

A second method for enhancing host cell viability comprises disruption of the CFTR protein coding sequence. For this purpose, a synthetic intron was designed for insertion between nucleotides 1716 and 1717 of the CFTR cDNA. This intron is especially advantageous because of its easily manageable size. Furthermore, it is designed to be efficiently spliced from CFTR primary RNA transcripts when expressed in eukaryotic cells. Four synthetic oligonucleotides were synthesized (1195RG, 1196RG, 1197RG and 1198RG) collectively extending from the Sph I cleavage site at position 1700 to the Hinc II cleavage site at position 1785 and including the additional 83 nucleotides between 1716 and 1717 (see FIG. 6). These oligonucleotides were phosphorylated with T4 polynucleotide kinase as described by Sambrook et al., mixed together, heated to 95° C. for 5 minutes in the same buffer used during phosphorylation, and allowed to cool to room temperature over several hours to allow annealing of the single stranded oligonucleotides. To insert the synthetic intron into the CFTR coding sequence and with reference to FIGS. 7A and 7B, a subclone of plasmid T11 was made by cleaving the Sal I site in the polylinker, repairing the recessed ends of the cleaved DNA with deoxynucleotide triphosphates and the large fragment of DNA Polymerase I and religating the DNA. This plasmid was then digested with Eco RV and Nru I and religated. The resulting plasmid T16-Δ5' extended from the Nru I site at position 490 of the CFTR cDNA to the 3' end of clone T16 and contained single sites for Sph I and Hinc II at positions corresponding to nucleotides 1700 and 1785 of the CFTR cDNA. T16-Δ5' plasmid was cleaved with Sph I and Hinc II and the large fragment was isolated by agarose gel purification. The annealed synthetic oligonucleotides were ligated into this vector fragment to generate T16-intron.

T16-intron was then digested with Eco RI and Sma I and the large fragment was isolated by agarose gel purification. T16-4.5 was digested with Eco RI and Sca I and the 790 bp fragment was also isolated by agarose gel purification. The purified T16-intron and T16-4.5 fragments were ligated to produce T16intron-2. T16-intron-2 contains CFTR cDNA sequences extending from the Nru I site at position 490 to the Sca I site at position 2818, and includes the unique Hpa I site at position 2463 which is not present in T16-1 or T16-intron-1.

Figure 8:
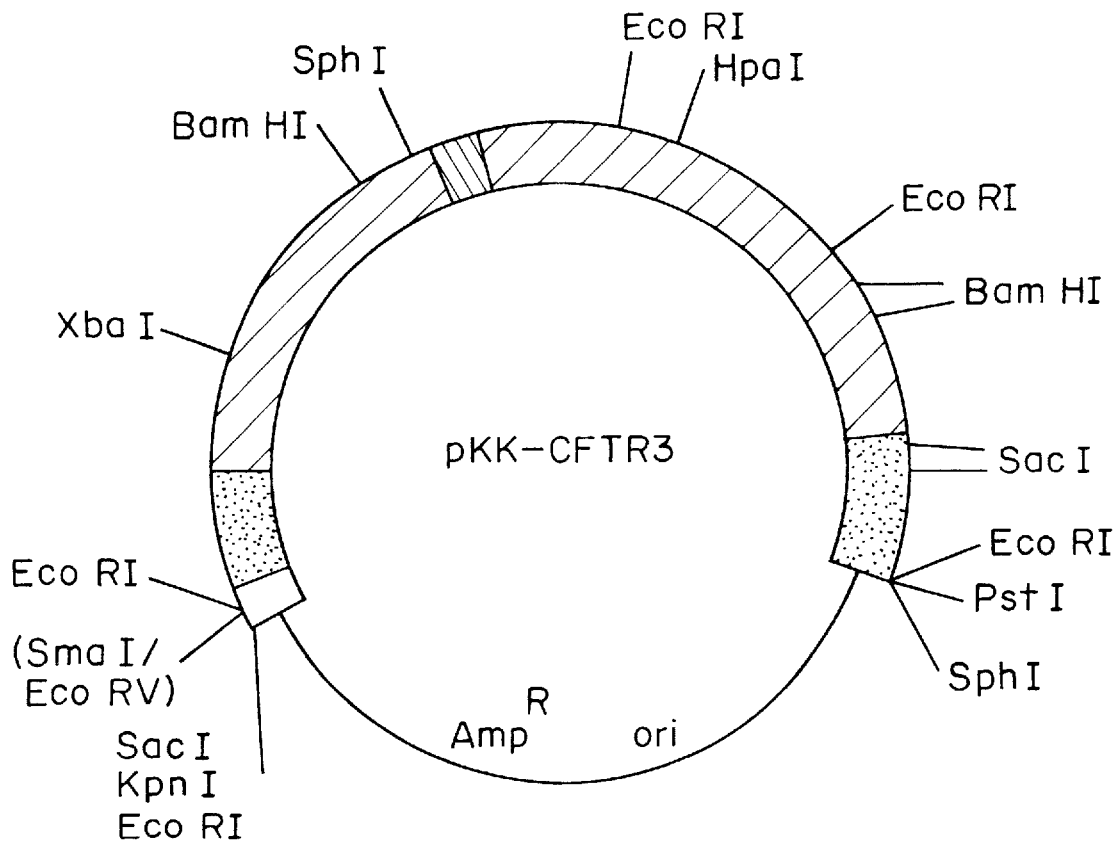
FIG. 8 shows a plasmid map of the CFTR cDNA pKK-CFTR3 containing an intron between nucleotides 1716 and 1717.

T16intron-2 was then cleaved with Xba I and Hpa I and the 1800 bp fragment was isolated by agarose gel purification. pKK-CFTR1 was digested with XbaI and Hpa I and the large fragment was also isolated by agarose gel purification and ligated with the fragment derived from T16-intron-2 to yield pKK-CFTR3, shown in FIG. 8. The CFTR cDNA within pKK-CFTR3 is identical to that within pSC-CFTR2 and pKK-CFTR2 except for the insertion of the 83 bp intron between nucleotides 1716 and 1717. The insertion of this intron resulted in improved growth characteristics for cells harboring pKK-CFTR3 relative to cells containing the unmodified CFTR cDNA in pKK-CFTR2.

EXAMPLE 4

In Vitro Transcription/Translation

In addition to sequence analysis, the integrity of the CFTR cDNA open reading frame was verified by in vitro transcription/translation. This method also provided the initial CFTR protein for identification purposes. 5 micrograms of pSC-CFTR2 plasmid DNA were linearized with Sal I and used to direct the synthesis of CFTR RNA transcripts with T7 RNA polymerase as described by the supplier (Stratagene). This transcript was extracted with phenol and chloroform and precipitated with ethanol. The transcript was resuspended in 25 microliters of water and varying amounts were added to a reticulocyte lysate in vitro translation system (from Promega). The reactions were performed as described by the supplier in the presence of canine pancreatic microsomal membranes (from Promega), using $^{35}$S-methionine to label newly synthesized proteins. In vitro translation products were analysed by discontinuous polyacrylamide gel electrophoresis in the presence of 0.1% SDS with 8% separating gels (Laemmli, 1970). Before electrophoresis, the in vitro translation reactions were denatured with 3% SDS, 8M urea and 5% 2-mercaptoethanol in 0.65M Tric-HCl, pH 6.8. Following electrophoresis, the gels were fixed in methanol:acetic acid:water (30:10:60), rinsed with water and impregnated with 1M sodium salicylate. $^{35}$S labelled proteins were detected by fluorograph. A band of approximately 180 Kd was detected, consistent with translation of the full length CFTR insert.

EXAMPLE 5

Elimination of Cryptic Regulatory Signals

Analysis of the of the DNA sequence of the CFTR has revealed the presence of a potential *E. coli* RNA polymerase promoter between nucleotides 748 and 778 which conforms well to the derived consensus sequence for *E. coli* promoters (Reznikoff and McClure, Maximizing Gene Expression, 1, Butterworth Publishers, Stoneham, Mass.). If this sequence functions as a promoter functions in *E. coli*, it could direct synthesis of potentially toxic partial CFTR polypeptides. Thus, an additional advantageous procedure for maintaining plasmids containing CFTR cDNAs in *E. coli* would be to alter the sequence of this potential promoter such that it will not function in *E. coli*. This may be accomplished without altering the amino acid sequence encoded by the CFTR cDNA. Specifically, plasmids containing complete or partial CFTR cDNA's would be altered by site-directed mutagenesis using synthetic oligonucleotides (Zoller and Smith, Methods Enzymol. 100, 468, 1983). More, specifically, altering the nucleotide sequence at position 748 from a T to C and at position 774 from an A to a G effectively eliminates the activity of this promoter sequence without altering the amino acid coding potential of the CFTR open reading frame. Other potential regulatory signals within the CFTR cDNA for transcription and translation could also be advantageously altered and/or deleted by the same method.

EXAMPLE 6

Cloning of CFTR in Alternate Host Systems

Although the CFTR cDNA displays apparent toxicity in *E. coli* cells, other types of host cells may not be affected in this way. Alternative host systems in which the entire CFTR cDNA protein encoding region may be maintained and/or expressed include other bacterial species and yeast. It is not possible a priori to predict which cells might be resistant and which might not. Screening a number of different host/vector combinations is necessary to find a suitable host tolerant of expression of the full length protein or potentially toxic fragments thereof.

EXAMPLE 7

Production of CFTR Mutants and Relevant Plasmid Constructions

Mutations were introduced into CFTR at residues known to be altered in CF chromosomes (ΔF508, ΔI507, R334W, S549I, G551D) and in residues believed to play an important role in the function of CFTR (K464M, F508R, N894,900Q, K1250M). CFTR encoded by these mutants was examined in COS-7 cells transfected with cDNA plasmids having the aforementioned alterations. Remarkably, it was surprisingly discovered that mature, fully glycosylated CFTR was absent from cells containing ΔF508, ΔI507, K464M, F508R and S549I cDNA plasmids. Instead, an unstable, incompletely glycosylated version of the protein was detected with an apparent molecular weight of 135 kd. Surprisingly, the immature, mutant versions of CFTR appear to be recognized as abnormal by a component of the post-translational intracellular transport machinery, and remain incompletely processed in the endoplasmic reticulum where they are subsequently degraded. Since mutations with this phenotype represent at least 70% of known CF chromosomes, we have discovered that the primary cause of cystic fibrosis is the absence of mature CFTR at the correct cellular location, see also FIGS. 10 and 12. As a result of this surprising result, this invention provides new approaches to the diagnosis and treatment of CF.

Recombinant DNA manipulations were performed according to standard methods (Sambrook et al., 1989). Oligonucleotide-directed mutagenesis of the CFTR cDNA was performed as described by Kunkel (1985). A plasmid vector for CFTR expression in mammalian cells was constructed by placing CFTR cDNA sequences from the Ava I site at position 122 in the cDNA sequence to the Sac I site at position 4620 into the unique BgI II site of the expression vector pSC-CEV1 using synthetic adaptor sequences. The resulting plasmid was called pMT-CFTR. In pMT-CFTR, expression of CFTR is controlled by the flanking mouse metallothionein-I promoter and SV40 early polyadenylation signal. The vector also contains an origin of replication from pSC101 (Cohen, 1973) for replication in *E. coli*, the β-lactamase gene and an SV40 origin of replication. For convenient site-directed mutagenesis of CFTR, the cryptic bacterial promoter within the CFTR cDNA of plasmid pTM-CFTR-3 (Gregory et al., 1990) was first inactivated by changing the T residue at nucleotide 936 to a C such that plasmids containing CFTR sequences could be maintained at high copy number without corresponding change in amino acid sequence. The CFTR cDNA was then inserted between the Apa I and Sac I sites of the high copy number vector pTM-1 (available from T. Mizukami, O. Elroy-Stein and B. Moss, National Institutes of Health) using a 5' flanking Apa I site common to pTM-CFTR-3 and pTM-1, and the Sac I site at position 4620 in the CFTR cDNA. This plasmid, pTM-CFTR-4, was used for all subsequent mutagenesis of the CFTR sequence. For expression in COS-7 cells, CFTR cDNA mutants constructed in pTM-CFTR-4 were digested with Xba I and BstX I and the 3.5 kb CFTR cDNA fragment was purified and placed between the unique Xba I and BstX I sites within the CFTR cDNA portion of pMT-CFTR. Transient expression of CFTR in COS-7 cells was performed essentially as described by Sambrook et al., 1989.

EXAMPLE 8

Production of CFTR and Protein Therapy

Protein therapy may be accomplished by using CFTR protein produced by host cells transformed or transfected with the CFTR cDNA of the present invention to correct the CF defect directly by introducing the protein into the membrane of cells lacking functional CFTR protein. This therapeutic approach augments the defective protein by addition of the wild-type molecule. The full length cDNA disclosed here can readily be used via conventional techniques to produce vectors for expression of the CFTR protein in a variety of well known host systems. Protein or membrane fragments purified or derived from these cells can be formulated for treatment of cystic fibrosis.

Recombinant CFTR can be made using techniques such as those reported by Numa (Harvey Lectures 83, 121 (1989) and references cited therein) for the synthesis of other membrane proteins under the direction of transfected cDNAs. It will be important to realize that toxicity can result in mammalian cells from over expression of membrane proteins (Belsham et al., Eur. J. Biochem. 156, 413 (1986)). Fortunately, to circumvent the potential toxicity of the protein product, vectors with inducible promoters (Klessig et al., Mol. Cell. Biol. 4, 1354 (1984)) can be advantageously used.

For example, for constitutive expression in mammalian cells, the full length CFTR cDNA clone is constructed so that it contains Xho I sites immediately 5' to the initiator methionine ATG and 3' to the terminator TAG. These sites are unique since there are no Xho I sites in the CFTR cDNA sequence. This facilitates incorporation of the DNA sequence encoding CFTR into the expression vectors of the types described below.

Those skilled in the art will recognize that many possible cell/vector systems have been used successfully for the high level expression of recombinant proteins. Several suitable systems are described below. Bovine Papilloma Virus (BPV) based vectors (Hamer and Walling, J. Mol. & Appl. Gen. 1, 273 (1982)) can be used to transform mouse C127 cells. C127 cells comprise an adenocarcinoma cell line isolated from a mammary tumor of an R111 mouse (ATCC: CRL 1616). Following the procedures of Hsiung et al. (J. Mol. & Appl. Gen. 2, 497 (1984)) and Reddy et al., (DNA 6, 461 (1987)), the BPV vector can be constructed in such a way as to express recombinant CFTR protein under control of the mouse metallothionine promoter and polyadenylation sequences. Once a construct containing the CFTR cDNA is made, it is then advantageously transfected into the C127 cells using standard calcium phosphate precipitation methods (Graham and Van der Eb, Virology 52, 456 (1973)). The transformed cells can then be selected by foci formation. A similar vector, in which the gene for neomycin resistance (Southern and Berg, J. Mol. & Appl. Gen. 1, 327 (1982)) has been inserted into the unique Sal I site, may advantageously also be super-transfected into the same cells and cells incorporating such vectors suitably selected with the antibiotic G418. This method conveniently decreases the time necessary to select for desired cell lines expressing the transfected gene product.

Another expression system employs vectors in which the cDNA is under control of the metallothionine gene promoter and the SV40 early polyadenylation signal. In addition, the mouse dihydrofolate reductase (DHFR) cDNA (Nunberg et al., Cell 19, 355 (1980)) is under control of the SV40 early promoter and polyadenylation signal. This vector is then ideally transfected into Chinese Hamster Ovary (CHO) cells (ATCC:CCL61) that are deficient in DHFR (Urlaub and Chasin, Proc. Natl. Acad. Sci. 77, 4216 (1980)). Transformed cells can be selected and the CFTR containing vector sequences amplified by culturing the cells in media containing the drug methotrexate.

Yet another example of an inducible expression system involves the use of vectors based upon the commercially available plasmid, pMAMneo (Clontech). pMAMneo contains a mouse mammary tumor virus promoter for expression of cloned genes. This promoter can be induced by treating transfected cells with glucocorticoids, such as dexamethasone, resulting in elevated expression of the cloned gene. The $Na^+/H^+$ antiporter is a membrane protein that is structurally very similar to the CFTR and has been successfully expressed with the pMAMneo vector (Sardet et al., Cell 56, 271 (1989)). Vectors based on pMAMneo, but containing low copy number E. coli origins of replication, could be used for inducible expression of CFTR in either C127 cells, CHO or other mammalian cells as described above.

Similarly, many suitable expression vector/host systems have been described for the expression of mammalian proteins in bacteria, fungi, insect and plant cells and in the milk of transgenic animals. One skilled in the art can modify these expression systems for the production of CFTR. For example, low copy number CFTR vectors, based upon the invention described herein, could be used to direct synthesis of CFTR protein in E. coli. To avoid toxicity due to expression of CFTR RNA or protein, the CFTR cDNA must be under the transcriptional control of a regulatable promoter. As an example of one such inducible expression system, the T7 RNA polymerase promoter within pSC-CFTR2 could be used to induce transcription of CFTR sequences in E. coli as described by Studier and Moffat (J. Mol. Biol. 189, 113 (1986). In order to maximize levels of CFTR protein expression after transcriptional induction, it would be necessary to introduce an E. coli ribosome binding site (Shine and Dalgarno, Nature 254, 43 (1975)) upstream of the CFTR initiator methionine. Prokaryotic organisms other than E. coli could also be used for expression of CFTR protein. For example, a membrane-bound phosphotriesterase has been successfully produced in Streptomyces lividans by Steiert et al. (Biotechnology 7, 65 (1989)).

Owing to the nature of CFTR glcosylation, the most preferred expression systems will utilize mammalian cells. Transient expression of CFTR can be accomplished using COS-7 cells as previously described in Example 7 and in subsequent examples.

Foreign proteins have been expressed using a variety of vectors in many different fungi. For example, van den Berg et al. (Biotechnology 8, 135 (1990)) have produced prochymosin in Kluyveromyces lactis, Loison et al. (Biotechnology 6, 72 (1988)) produced hirudin in Saccharomyces cerevisiae, and Cregg et al. (Biotechnology 5, 479 (1987)) have produced hepatitis B surface antigen in Pichia pastoris.

For insect cells, the β-adrenergic receptor, a membrane protein, has been expressed using a baculovirus expression vector (George et al., Biochem. Biophys. Res. Comm. 163, 1265 (1989)). CFTR could be produced in insect cells by obvious modification of this system.

CFTR could be expressed in plants by modification of the techniques of Hiatt et al. (Nature 342, 76 (1989)) which have demonstrated the production of the immunoglobulin heavy and light chains in tobacco and other plants.

Techniques for the production of foreign proteins in the milk of transgenic animals have also been described in EPA 0264,166, fully incorporated herein. These techniques can readily be modified for production of CFTR in the milk of mammals. Similarly, the invention described herein enables the use of techniques known to those skilled in the art for the production of a transgenic animal model for cystic fibrosis. Such a CF animal model could be advantageously employed to screen for suitable pharmacological therapeutic agents as later described.

EXAMPLE 9

Characterization of the CFTR Protein

A. Isolation of CFTR.

CFTR is a membrane protein having an amino acid sequence which contains regions with extensive hydrophobic character. In order to purify CFTR as a functional protein it will be important to accomplish the solubilization of the CFTR from its native membrane such as through the use of detergents.

Conditions for the solubilization of CFTR from its natural lipid environment can be advantageously determined using whole cells, or membrane preparations prepared from cells which express CFTR. As will be readily understood, initial solubilization experiments will involve screening a variety of detergents at varying concentrations in order to find conditions that preferably achieve optimal solubilization of the CFTR. Briefly, packed membrane pellets are resuspended in detergent solution, gently homogenized, and the insoluble material removed by centrifugation at 100,000 g for one hour. The degree of solubilization achieved is ideally monitored immunologically. Potential detergents include, but are not limited to, CHAPS (3-(3-cholamidopropyl) dimethylammonio)-1-pro(anesulfonate) (Borsotto M., et al., J. Biol. Chem. 260, 14255 (1985)), Hamada and Tsuro, J. Biol. Chem. 263 1454 (1988)), n-octyl glucoside (Landry et al., Science 244, 1469 (1989)); lubrol (Smigel, J. Biol. Chem. 261, 1976 (1986)); Agnew et al., BBRC 92, 860 (1980)); Triton X-100 (Hartshorne and Catterall, J. Biol. Chem. 259, 1667 (1984)); and Triton X-114 (Bordier, J Biol Chem 256, 1604 (1981)). The initial detergent solubilized CFTR solution can also be diluted into an appropriate concentration of detergent or detergent/lipid (Agnew and Raftery, Biochemistry 18, 1912 (1979)) to achieve stabilization of the CFTR. Compounds known to stabilize proper folding of membrane proteins, sometimes referred to as ozmolytes, can also be used. Such stabilization agents include polyols such as glycerol, sugars and amino acids (Ambudkar and Maloney, J. Biol. Chem. 261, 10079(1986)). In addition, protease inhibitors against the four major classes of proteases are advantageously present throughout these procedures (Hartshorne and Catterall, J. Biol. Chem. 259, 1667 (1984)) and would include, for example, phenylmethylsulfonyl fluoride for serine proteases; iodoacetamide for thiol proteases; 1,10-phenanthroline for metalloproteases; and pepstatin A for proteases with activated carboxylic acid groups. Ideally, studies should be carried out in which the concentrations and relative proportions of detergent, lipid and ozmolyte are varied together with other buffer conditions in order to identify optimal conditions to preserve and stabilize the CFTR. For example, Agnew and Raftery varied the ratio of various detergents and lipids and determined that a 7 to 1 ratio of lubrol to phosphatidylcholine stabilized the solubilized voltage sensitive sodium channel for further purification. Similarly, Hartshorne and Catterall found that the presence of 0.25% egg phosphatidylcholine produced a more stable preparation and an increased recovery during purification of the sodium channel solubilized with Triton X-100. To determine the functional integrity of the solubilized protein may require reconstitution of the protein into liposomes using the procedure of Example 11, followed by introduction into cells and testing using the ion efflux assays of Example 14.

B. Immunoprecipitations and protein phosphorylation using protein kinase A.

The procedures employed for isotopic labeling of cells, preparation of cell lysates, immunoprecipitation of proteins and SDS-polyacrylamide gel electrophoresis were as described by Cheng et al., 1988 and Gregory et al., 1990. CFTR was phosphorylated in vitro with protein kinase A essentially as described by Kawata et al. (1989). Briefly, immunoprecipitates were incubated with 20 ng of protein kinase A (Sigma) and 10 $\mu$Ci of ($\gamma$-$^{32}$P)ATP in 50 $\mu$l of kinase buffer (50 mM Tris-HCl, pH 7.5, 10 mM $MgCl_2$ and 100 $\mu$g/ml bovine serum albumin) at 30° C. for 60 minutes. The reaction was stopped by the addition of 0.5 ml RIPA buffer (50 mM Tris-HCl, pH 7.5, 150 mM NaCl, 1% Triton X-100, 1% sodium deoxycholate and 0.1% sodium dodecyl sulphate). The procedure for Cleveland digestion was performed as described by Cleveland et al. (1977) with modifications (Cheng et al., 1988).

C. Digestion with glycosidases.

Figure 9:
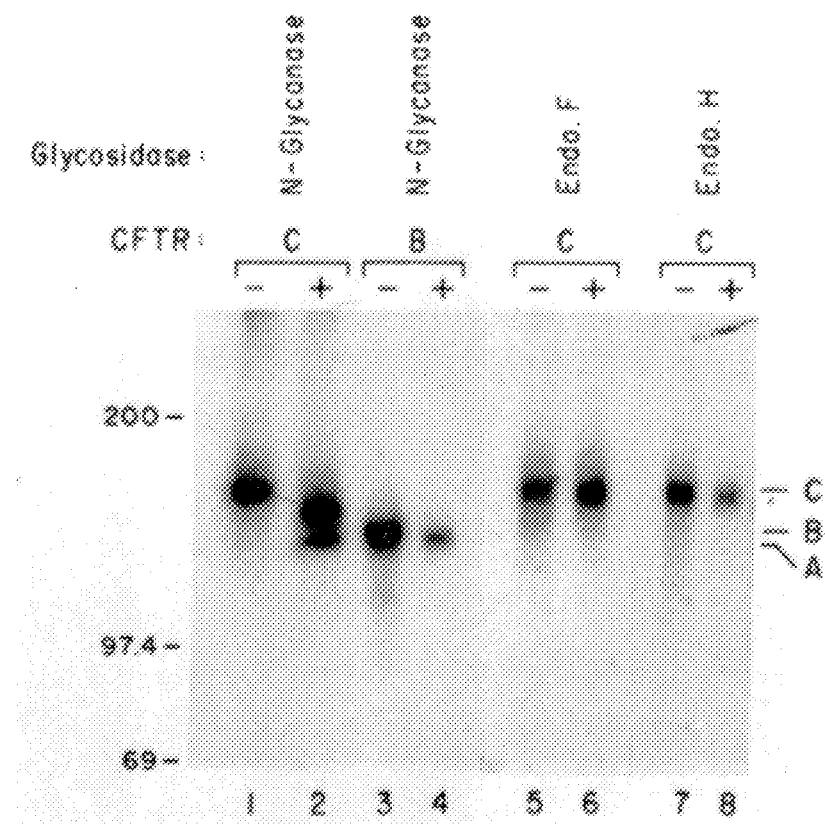
FIG. 9 shows treatment of CFTR with glycosidases.

The glycosidases N-GLYCANASE® enzyme, O-GLYCANASE® enzyme, endoglycosidase H and endoglycosidase F were obtained from Genzyme Corporation. Conditions for digestion with the respective enzymes were as specified by the manufacturer except incubations were performed at 37° C. for 4 h only. All digestions were performed on CFTR which had been purified by immunoprecipitation and separation on polyacrylamide gels (see Example 10). CFTR bands B and C were eluted from the gels by maceration of the gel pieces in extraction buffer (50 mM ammonium bicarbonate, 0.1% SDS and 0.2% $\beta$-mercaptoethanol). Referring to FIG. 9, bands B and C were immunoprecipitated from T84 cells and phosphorylated in vitro using protein kinase A and ($\gamma$-$^{32}$P)ATP. The CFTR proteins were extracted from the SDS-polyacrylamide gels, subjected to no treatment (lanes 1, 3, 5 and 7) or were incubated with N-GLYCANASE® enzyme (lanes 2 and 4), endoglycosidase F (lane 6) or endoglycosidase H (lane 8). Samples were separated by electrophoresis and analysed by autoradiography. Exposure was for 24 h.

D. Pulse-chase studies.

Figure 11A:
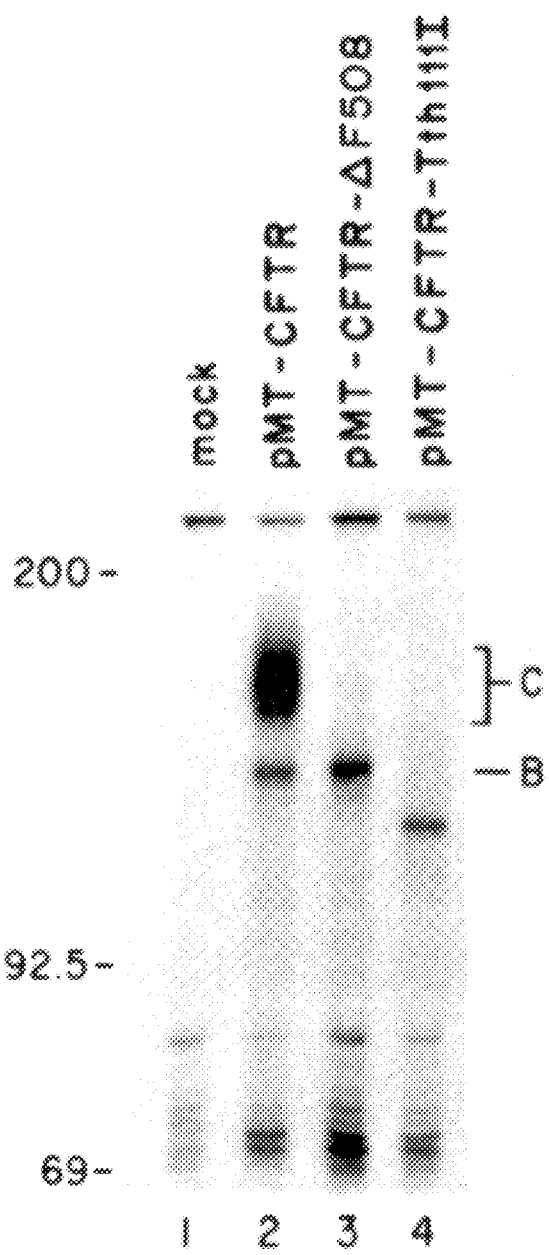
FIGS. 11A and 11B show pulse-chase labeling of wild type and ΔF508 mutant CFTR in COS-7 transfected cells.
Figure 11B:
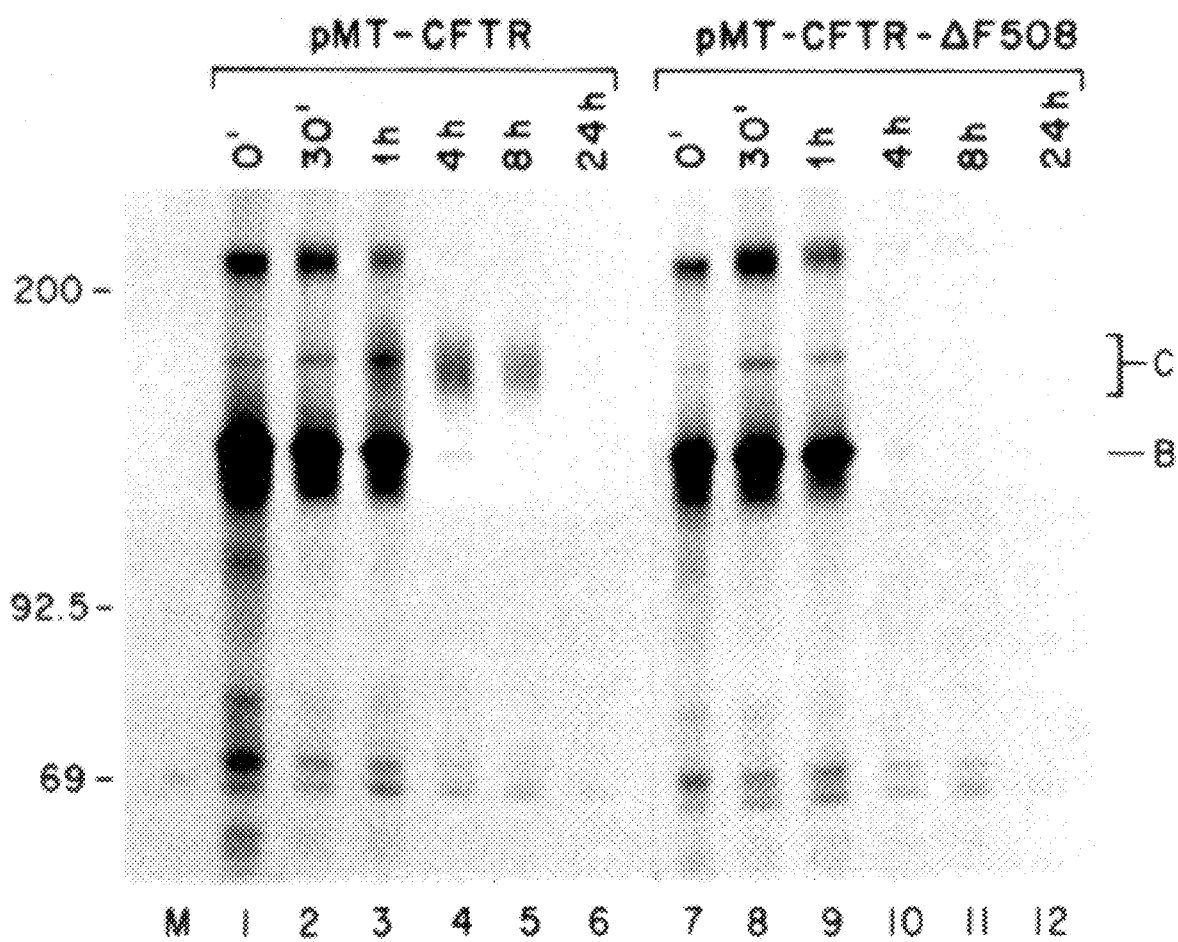
Figure 12A:
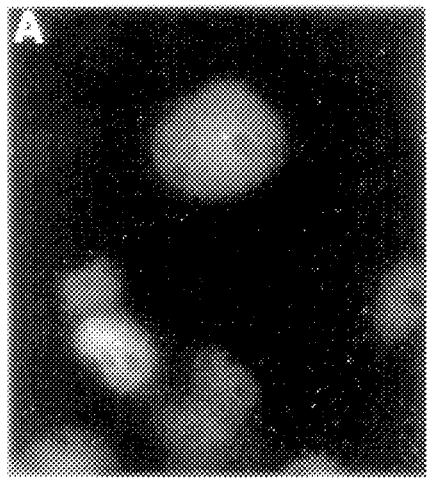
FIG. 12 shows immunolocalization of wild type and ΔF508 mutant CFTR; and COS-7 cells transfected with pMT-CFTR or pMT-CFTR-ΔF508.
Figure 12B:
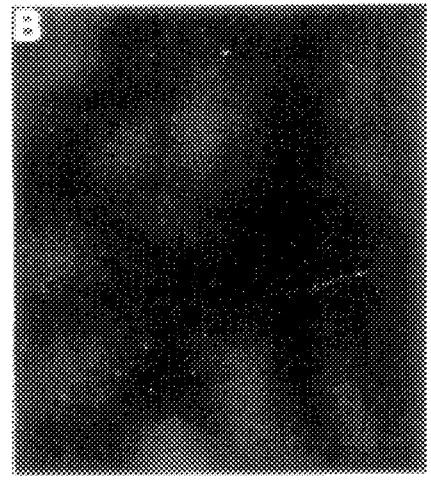
Figure 12C:
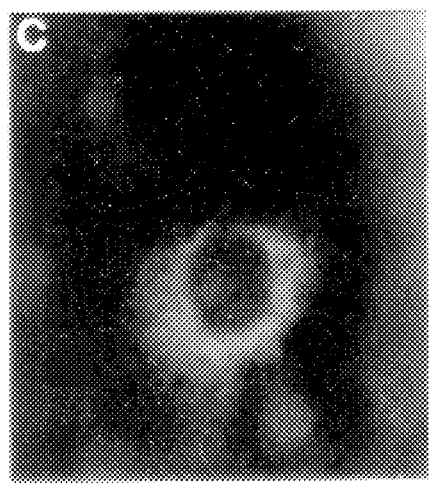
Figure 12D:
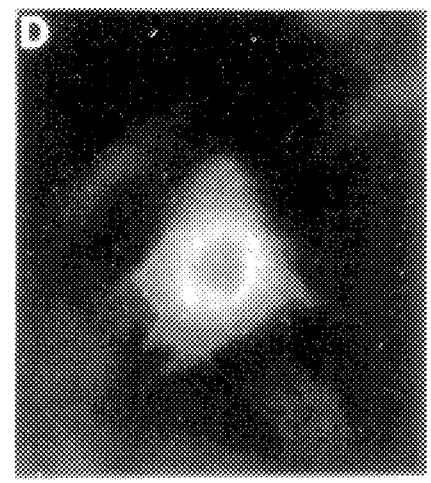

Six 90 mm dishes of COS-7 cells were transfected with either pMT-CFTR or pMT-CFTR-$\Delta$F508. To avoid dish to dish variation in transfection efficiency, at 12 h post-transfection, the cells were harvested by trypsinization and re-distributed among six 90 mm dishes. Following 18 h of incubation, the cells were washed twice with DME media (lacking methionine) and starved for 30 minutes at 37° C. ($^{35}$S)methionine (250 $\mu$Ci/ml) was then added to each dish and the plates labeled for 15 minutes at 37° C. At the end of the 15 minutes, the cells were washed twice with growth media, maintained in growth media and then chased for various times up to 24 h. Referring to FIG. 11A, COS7 cells were mock transfected (lane 1) or transfected with pMT-CFTR (lane 2), pMT-CFTR-$\Delta$F508 (lane 3) and pMT-CFTR-Tth111 1 (lane 4). 48 h post-transfection, the cells were labeled for 12 h with ($^{35}$S)methionine. CFTR from these lysates were immunoprecipitated with the monoclonal antibody mAb 13-1 (see Example 11) and then analyzed on a SDS-polyacrylamide gel. The gel was fluorographed and exposed for 4 h. In FIG. 11B COS-7 cells were either transfected with pMT-CFTR (lanes 1–6) or pMT-CFTR-$\Delta$F508 (lanes 7–12). At 48 h post-transfection, the cells were labeled for 15 minutes with ($^{35}$S)methionine. After being labeled, the cells were either harvested immediately or rinsed several times with labeling media, transferred to standard growth media and then harvested at various times thereafter. The lysates prepared were immunoprecipitated with mAb 13-1 and analyzed on a SDS-polyacrylamide gel. The fluorograph gel was exposed for 6 h.

E. Immunofluorescence microscopy.

Indirect immunofluorescence was performed essentially as described by Kalderon et al. (1985). COS7 cells which had been transfected with CFTR-containing cDNAs (see Example 7) were transferred onto glass coverslips at 12 h. Following a further 18 h incubation at 37° C., the cells were fixed in 3.7% formaldehyde in phosphate buffered saline (30 minutes at room temperature), permeabilized with 1% Nonidet P40 (15 minutes at room temperature) and incubated with the monoclonal antibody mAb 13-1 (see Example 11) followed by FITC-conjugated goat anti-mouse IgG (Cappel Labs.). The cover slips were mounted using 50% glycerol in phosphate buffered saline and viewed using a Zeiss Axiopian microscope. With reference to FIG. 12, 48 hours after transfection, the cells were fixed and stained using the monoclonal antibody mAb 13-1 (Example 11) or 423 (specific for SV40 Large-T antigen) as first antibody. The second antibody was fluorescein-conjugated goat anti-mouse IgG. The localization of the various CFTR proteins were visualized by immunofluorescence microscopy. Micrograph (A) shows nuclear staining of SV40 Large-T antigen using the monoclonal antibody 423 (Harlow et al., 1981); (B) shows pMT-CFTR incubated with mAb 13-1 in the presence of excess fusion protein; (C) shows pMT-CFTR-$\Delta$F508 incubated with mAb 13-1 and (D) shows pMT-CFTR incubated with mAb 13-1.

EXAMPLE 10

Purification of the CFTR Protein

Utilizing the solubilized CFTR protein from Example 9, one may purify the CFTR utilizing purification procedures which have been employed previously with similar membrane proteins. Although proteins with multiple membrane spanning domains have been purified using conventional techniques (Catterall, Science 242 50 (1988)), the generation of specific antibodies has allowed other investigators to develop rapid and simple purification schemes for P-glycoprotein (Hamada and Tsuro, J. Biol. Chem. 263 1454 (1988)), and sodium channels (Casadei et al., J. Biol. Chem. 261 4318 (1986); Nakayama et al., Proc. Natl. Acad. Sci. 79 7575 (1982)). Thus, the production of CFTR specific antibodies (see Example 11) could facilitate the purification of the CFTR molecule and allow its purification away from the relatively high level of contaminants expected in the starting solubilized preparation.

For example, antibodies produced against an extracellular or other domain of the CFTR could be screened to select therefrom an antibody having a suitably high binding coefficient appropriate for use in the purification scheme. The selected antibody is ideally immobilized on a variety of commercially available resins including CNBr activated Sepharose, Affi-Gel 10, Reacti-Gel CDI and Amino-Link resins and tested for immobilized antibody capacity. Optimal conditions for binding CFTR to the column, washing the column to remove contaminants, and eluting the purified protein can then be determined using conventional parameters as the starting point and testing the effect of varying the parameters. It will be recognized that effective wash and elution conditions will significantly impact the degree of purification obtained. Extensive washing in the presence of stabilizers plus higher salt and differing detergents may be utilized to remove nonspecifically absorbed proteins. Elution may then be advantageously carried out either using specific peptide elution if one has antibodies to CFTR peptides. (Courtneige et al., Cold Spring Harbor Conf on Cell Prolif. and Cancer 2 123 (1984)), or alternatively by chaotropic agents such as potassium thiocyanate or by lowering the pH followed by immediate pH neutralization of the eluted fractions.

Although it is likely that immunoaffinity chromatography would provide a significant purification and provide protein of sufficient purity for research studies and drug screening, such an approach alone may not provide adequate protein purity to qualify the CFTR protein as a clinical grade therapeutic agent. Thus, to purify the protein further, or in the case that immunoaffinity chromatography was unsuccessful, one could evaluate additional chromatographic approaches to select an optimal chromatography procedure to obtain the desired purity. For example, ligand affinity (Landry et al., Science 244 1469 (1989); Smigel, J. Biol. Chem. 261 1976 (1986)), lectin (Curtis and Catterall, Biochemistry 23 2113 (1984)), anion exchange (Hartshorne and Catterall, Proc. Natl. Acad. Sci. 78 4620 (1981)), hydroxylapatite (Hartshorne and Catterall, J. Biol. Chem. 259 1667 (1984)), and gel filtration (Borsotto et al., J. Biol. Chem. 260 14255 (1985)) chromatography procedures have been used in purification schemes for this class of membrane bound proteins. Since the CFTR protein contains a nucleotide binding domain, it will likely bind to resins such as Cibicron blue and may be specifically eluted with nucleotides (Lowe and Pearson, Methods in Enzymology 104 97 (1984)). The accessibility of the nucleotide binding domain in the solubilized form would have to be determined empirically. The predicted protein sequence for the CFTR contains a carbohydrate attachment site at amino acid 894. Since it has now been shown that the CFTR protein is a glycoprotein, the use of lectin chromatography is a likely route to purify CFTR.

EXAMPLE 11

Preparation of CFTR Protein Specific Antibodies

Monoclonal antibodies MAb 13.1 and MAb 13.2, specific for predetermined regions or epitopes of the CFTR protein, were prepared using the following cloning and cell fusion technique. A mouse was immunized with the polypeptide produced from Exon 13 of the CFTR protein fused to β-galoctosidase, the fusion protein being obtained as described in Mole and Lane, DNA Cloning Volume III: A Practical Approach (1987), to induce an immune response. The immunization procedure required injecting a mouse with 10 micrograms of immunogen in 10 microliters of PBS emulsified in 30 microliters of Freunds complete adjuvant (Gibco #660-5721AS). This procedure was repeated four times at intervals of from 1 to 28 days over a 57 day period. The mouse was then injected with 50 micrograms of immunogen in 50 microliters of PBS four times over a three day period. Vasodilation was induced by warming the mouse for 10 minutes with a desk lamp. The mouse was sacrificed by $CO_2$ intoxication and a splenectomy was performed.

After immunization was carried out, the β-lymphocytes of the immunized mice were extracted from the spleen and fused with myeloma cells using the well known processes of Koehler and Milstein (Nature, 256 (1975),495–497) and Harlow and Lane, Antibodies, A Laboratory Manual, Cold Spring Harbor Laboratory, New York (1988), respectively. The resulting hybrid cells were cloned in the conventional manner, e.g. using limiting dilution, and the resulting clones, which produce the desired monoclonal antibodies, cultured. Two most preferred antibodies produced by this process were MAb 13.1 and MAb 13.2, specific for Exon 13.

The monoclonal antibodies, MAb 13.1 and MAb 13.2, may be used in their complete form or as fragments thereof (e.g. Fab or F(ab')$_2$ fragments) providing they exhibit the desired immunological reactivity with CFTR or the desired CFTR domain. The term "monoclonal antibody" as used herein therefore also includes such fragments. The monoclonal antibody is ideally used in an immobilized form, and is most preferably immobilized on a resin substrate, for purification of the CFTR protein from other contaminants. The antibodies can also be advantageously used as part of a kit to assay for the presence of the CFTR protein in biological samples such as fluids or on the surface of cells.

Hybridomas producing monoclonal antibodies MAb 13.1 and MAb 13.2 prepared according to this procedure have been deposited with the American Type Culture Collection (ATCC) under the terms of the Budapest Treaty, and assigned accession numbers: ATCC 10565 and ATCC 10566.

EXAMPLE 12

CFTR Production Results from Cells Transformed with Various CFTR Genes including Mutants A. CFTR from T84 cells.

Previous examples show that CFTR can be detected in T84 cells by adding ($\gamma$-$^{32}$P)ATP and protein kinase A to immunoprecipitates formed using antibodies raised against CFTR (see also Gregory et al., 1990). Band B, and large amounts of band C were detected by this method (see FIG. 9). Partial proteolysis fingerprinting showed that the T84 cell derived material and that produced in a cell-free system directed by CFTR RNA were indistinguishable.

FIG. 9 demonstrates that band C is CFTR modified by addition of N-linked carbohydrate. Upon treatment with N-GLYCANASE® enzyme, band C, immunoprecipitated from T84 cells and phosphorylated in vitro, is converted to band A. Treatment with O-GLYCANASE® enzyme, endoglycosidase H or endoglycosidase F enzymes had no effect (FIG. 9). Because a band of intermediate molecular weight was also detected upon treatment with N-GLYCANASE® enzyme, these results can be interpreted to mean that CFTR bears two complex carbohydrate side chains possibly of the tri- or tetra-antennary type. N-GLYCANASE® enzyme treatment of band B also yielded band A (FIG. 9) (see also Gregory et al., 1990). The shift in apparent molecular weight on polyacrylamide gels in going from band A to band C seems large (20K) but whether this represents addition of unusually large side chains, or merely results from anomalous migration in SDS-polyacrylamide gels is unknown. It is postulated that glycosylation of band C is probably also responsible for its migration as a diffuse band as opposed to the sharp appearance of bands A and B.

B. ΔF508 does not Produce Mature CFTR.

Figure 10A:
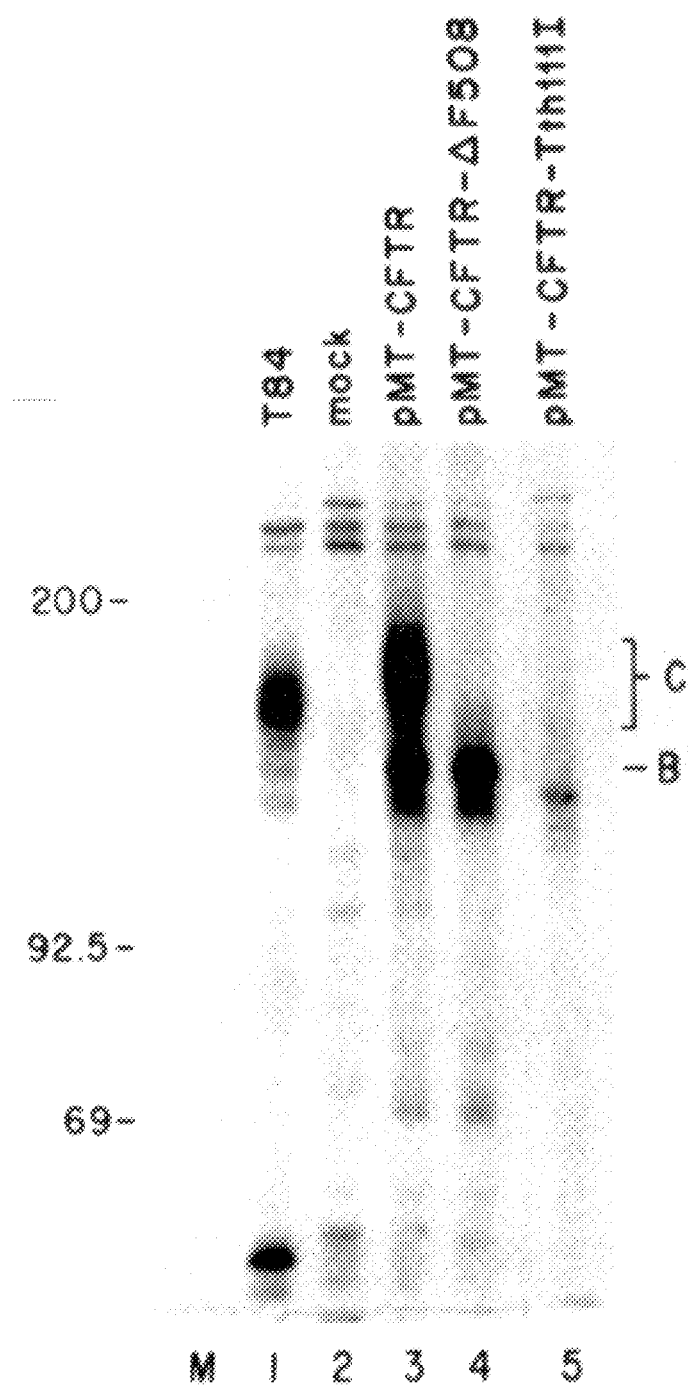
FIGS. 10A and 10B show an analysis of CFTR expressed from COS-7 transfected cells.
Figure 10B:
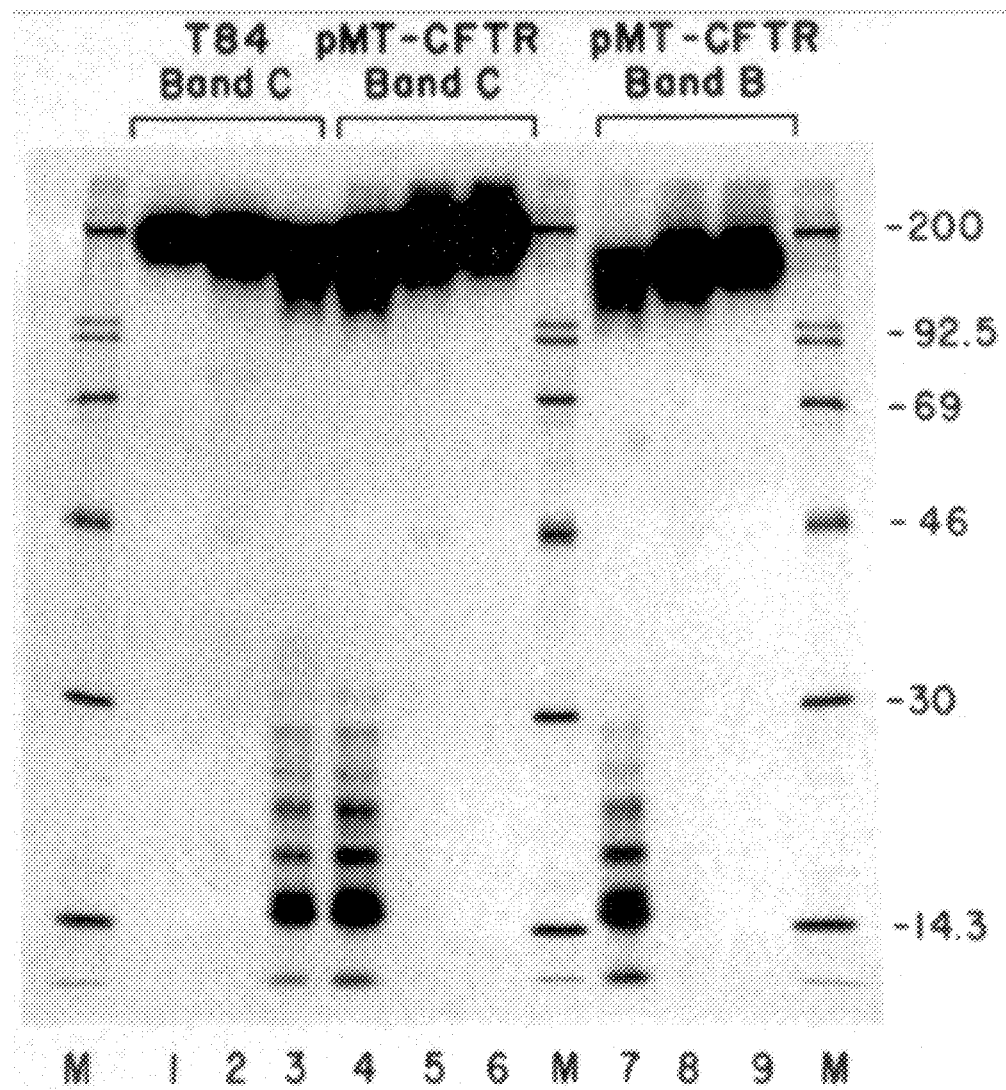

Recombinant CFTR has been expressed utilizing a vaccinia virus-infected HeLa cell system (see also Gregory et al., 1990; Rich et al., 1990). Because of the short infection cycle of vaccinia virus, longer term expression was studied in transfected COS7 cells (see Example 7). With reference to FIG. 10A, COS-7 cells were either mock transfected (lane 2), transfected with wild type CFTR (pMT-CFTR—lane 3) or the mutants pMT-CFTR-ΔF508 (lane 4) and pMT-CFTR-Tth111 1 (lane 5). Lysates were prepared 48 h post-transfection, phosphorylated in vitro with protein kinase A and ($\gamma$-$^{32}$P)ATP and analyzed on a SDS-polyacrylamide gel. Lane 1 contains lysate from T84 cells. The positions of bands B and C are indicated on the right margin. Autoradiography was for 2 h. With reference to FIG. 10B, the $^{32}$P in vitro labeled bands C from T84 cells (lanes 1–3) and from COS7 cells transfected with pMT-CFTR (lanes 4–6) and band B from cells transfected with pMT-CFTR (lanes 7–9) were excised from the gel and digested with increasing amounts of S. aureus V8 protease. Proteins in lanes 2, 5 and 8 were digested with 0.017 μg/μl of S. aureus V8 protease and those in lanes 3, 4 and 7 with 0.17 μg/μl of enzyme. Lanes 1, 6 and 9 were untreated samples. Exposure time was two days.

Thus, FIG. 10A shows CFTR produced in cells transfected with an expression plasmid (pMT-CFTR) containing a full length CFTR coding sequence expressed from a mouse metallothionein promoter. Using the $^{32}$P in vitro labeling technique and affinity purified polyclonal antibody to exon 13 fusion protein (see also Examples 10, 11, 17 and also Gregory et al., 1990), band C was readily detected in transfected cells, as well as smaller amounts of band B (lane 3). COS7 cell band C migrated more slowly than the CFTR from T84 cells (lane 1) but FIG. 10B shows partial proteolysis fingerprints that confirm that the proteins are indeed related. Presumably, the glycosylation pattern of human colon and simian kidney cells is sufficiently different to alter the mobility of band C.

FIG. 10A also shows that COS7 cells transfected with vectors containing a ΔF508 cDNA produced band B but, unexpectedly, they did not contain band C (lane 4). Similarly, a mutant CFTR truncated by insertion of a frame shift mutation at the Tth111 1 site (which resulted in the synthesis of a 1357 amino acid protein) encoded a truncated version of band B of predicted molecular weight but also lacked the band C equivalent (lane 5).

To confirm this data, metabolically labeled COS-7 cells were used. After the cells were labeled with ($^{35}$S)methionine for 16 hours, they were lysed and immunoprecipitated with monoclonal antibody mAb 13-1 (raised against exon 13 fusion protein) (see Example 11). FIG. 11A shows that band B was labeled in COS-7 cells transfected with wild type (lane 2) and ΔF508 cDNA (lane 3) but surprisingly, that labeled band C was totally absent in the mutant cDNA transfected cells.

FIG. 11B shows the result of a pulse-chase experiment in which COS-7 cells, transfected with wild type and ΔF508 cDNA vectors pursuant to Example 7, were labeled for 15 mins and chased over a 24 hour period. Wild type band B chased into band C such that by 4 hours after labeling, very little band B remains (lane 4). Mature CFTR was observed at 1, 4 and 8 h post labeling but by 24 hours, little remaining labeled material was detected. By contrast, although ΔF508 band B was metabolized with approximately the same half-life as wild type, no band C appeared.

Not all labeled band B in pulse labeled wild type cDNA transfected cells appeared to be processed to the fully glycosylated band C. One interpretation of this finding is that recombinant cells contained such large amounts of CFTR that the machinery responsible for further post translational processing was saturated. Under these circumstances, excess material may be degraded. An alternative explanation is that during the chase period, so much unlabeled CFTR accumulated that insufficient antibody was present to capture all the labeled protein. Studies with vaccinia virus-infected HeLa cells synthesizing CFTR showed that very little bond C material was detected in a 1 h labeling period. This labeling pattern is consistent with the kinetics shown here.

C. Immunofluorescence Studies.

The absence of mature CFTR in ΔF508 cDNA transfected COS-7 cells implies that the deletion caused a structural alteration that somehow prevented maturation of the carbohydrate in the Golgi. This could result because transport from the endoplasmic reticulum to the Golgi was inhibited or because modification was inhibited even though transport was normal. It was hypothesized that if protein transport were inhibited it might be possible to detect a difference in location of mutant and wild type recombinant CFTR by immunofluorescence.

FIG. 12 shows Immunofluorescence photomicrographs of COS-7 cells transfected with wild type and ΔF508 CFTR cDNAs using monoclonal antibody mAb 13-1. That the fluorescence detected was CFTR is indicated by the previous characterization of the monoclonal antibody, by the absence of signal in non-transfected cells (background cells in FIGS. 12c and 12d) and because the reaction was inhibited by exon 13 fusion protein (FIG. 12b) but not irrelevant fusion protein. FIGS. 12c and 12d show that the subcellular distribution of wild type and ΔF508 CFTR was different. The ΔF508 signal appeared localized to the perinuclear region whereas the wild type CFTR signal was more diffuse. The pattern observed with wild type suggests a wide-spread distribution possibly including the plasma membrane.

Because the distribution of CFTR in recombinant cells overexpressing the protein may not be typical, subcellular localization of wild type and ΔF508 was not refined. Subcellular distribution of ΔF508 CFTR was different from wild type.

D. Other Mutations Prevent Maturation of CFTR.

To study the maturation of CFTR in more detail, additional site specific mutations within the cDNA coding sequence were constructed. A naturally occurring deletion mutation at residue 507 was created by removing the codon for isoleucine (Kerem et al.,1990). To examine the role of nucleotide binding within the domain including ΔF508, the highly conserved lysine at residue 464 (Riordan et al., 1989) was changed to methionine. The equivalent mutation was also made within the second nucleotide binding domain (K1250M) and both asparagine residues (at 894 and 900) were changed to glutamine to which carbohydrate is predicted to be attached (N894,900Q) (Riordan et al., 1989).

Figure 13:
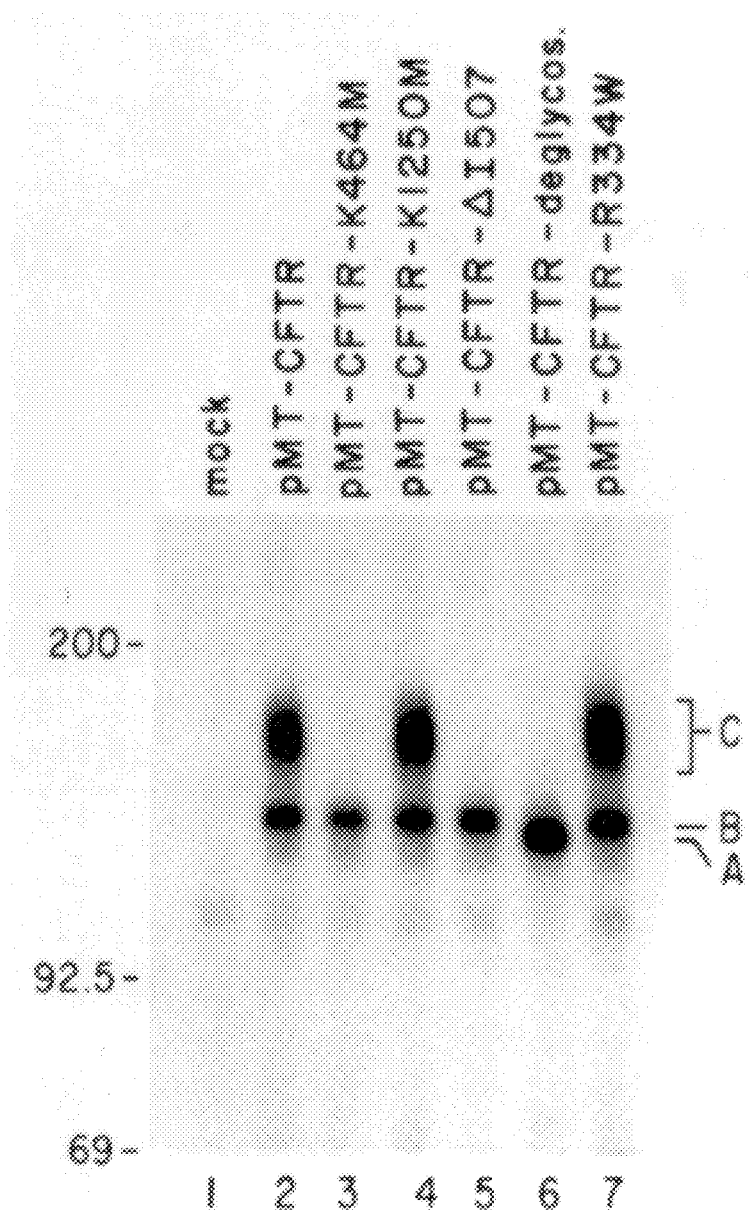
FIG. 13 shows an analysis of mutant forms of CFTR.

Vectors containing each of these mutations were constructed and separately transfected into COS-7 cells. With reference to FIG. 13, expression vectors containing wild type CFTR (pMT-CFTR—lane 2) and those containing the mutants pMT-CFTR-K464M (lane 3), pMT-CFTR-K1250M (lane 4), pMT-CFTR-ΔI507 (lane 5), pMT-CFTR-N894, 900Q (lane 6, marked as pMT-CFTR-deglycos.) and pMT-CFTR-R334W (lane 7) were transfected into COS7 cells. Lane 1 is COS-7 cells which had been mock transfected. Lysates were prepared 48 h post-transfection and the immunoprecipitates formed using pAb Ex13 were labeled in vitro using protein kinase A and ($\gamma$-$^{32}$P)ATP. The positions of bands A, B and C are indicated on the right margin. Autoradiography was for 2 h.

FIG. 13 shows that using the in vitro kinase assay, ΔI507 cDNA transfected cells, like their ΔF508 counterparts, lacked band C (lane 5). N894,900Q produced neither band B or C, but instead yielded a band of slightly increased mobility which was interpreted to be the CFTR primary translation product, band A, of apparent molecular weight 130 kd (lane 6). This confirmed that it was the addition of N-linked carbohydrate to CFTR that caused the mobility shifts resulting in bands B and C. Individual mutations in each of the two sites was required to establish unequivocally that both Asn894 and Asn900 are glycosylated and based on the N-GLYCANASE® enzyme results, this seems likely.

K464M cDNA transfected cells, like their ΔI507 and ΔF508 nucleotide binding domain 1 mutant counterparts, contained no band C (lane 3). Surprisingly, however, the equivalent mutation in the conserved lysine of the second nucleotide binding domain did not prevent maturation (lane 4). Another rare but naturally occurring mutation associated with CF occurs at residue Arg334 within transmembrane domain 6 (X. Estivill, personal communication). This mutation, R334W, did not prevent maturation of recombinant CFTR band C, (Lane 7).

Table 1 summarizes data obtained with all the mutants including two other naturally occuring CF associated mutations S549I and G551D. These were from a second cluster of mutations within the first nucleotide binding domain, in this case within exon 11 (Cutting et al., 1990a: Kerem et al., 1990). Also included is F508R, in which the residue at 508 was changed rather than deleted. Surprisingly, the results using these mutants showed S549I CFTR does not mature but G551D does. The mutation of phenylalanine 508 to arginine also resulted in CFTR that did not mature.

EXAMPLE 13

Intracellular Characterization of CFTR

A. Endoplasmic reticulum interactions.

Based on the discoveries of this invention, nascent CFTR interacts first with the endoplasmic reticulum and is then glycosylated at least one of Asn residues 894 and 900. The native molecule is then transported to the Golgi where carbohydrate processing to complex-type glycosylation occurs. Finally, at least some of the mature glycosylated molecule is thereafter transported to the plasma membrane.

It is now reasonably well established that the endoplasmic reticulum possesses a mechanism that prevents transport of mutant, misfolded or incorrectly complexed versions of proteins otherwise destined for further processing (Lodish, 1988; Rose and Doms, 1988; Pelham, 1989; Hurtley and Helenius, 1989; Klausner and Sitia, 1990). If this quality control mechanism operates on CFTR, it would prevent transport to the Golgi and consequently, further modification of several of the mutants reported here. As a result, the unmodified mutant versions of the protein either would not exit the endoplasmic reticulum and would subsequently be degraded therein, or alternatively, they would be transported to the lyosomes for degradation.

It is not clear how the quality control mechanism recognizes the difference between wild-type and those mutant versions of CFTR which were not further processed. One obvious mechanism would be that an alteration in structure of the molecule is detected. Indeed, gross changes in structure of the first nucleotide binding domain (and perhaps in consequence of the whole molecule) might be expected following deletion of phenylalanine 508 (Hyde et al., 1990; Manavalan and Dearborn, personal communication). However, it is not clear how this change in structure would be detected by a mechanism located, for example, in the lumen of the endoplasmic reticulum, since the domain bearing the mutation, (if the present model for CFTR is correct), would lie on the cytosolic side of the membrane. Perhaps the structural change is transmitted across the membrane or perhaps the sensing mechanism does not recognize CFTR directly, but rather detects a protein with which it is complexed. In this case, all mutations within CFTR that prevent complex formation also prevent intracellular transport. Yet another mechanism would be that nascent CFTR has basal activity in the endoplasmic reticulum and that mutations that disrupt this activity are sensed by the quality control mechanism. Perhaps some activity of CFTR is necessary for its maturation and by this means, enzymatically inactive proteins are marked for degradation. Irrespective of the mechanism of discrimination, the time course of synthesis of both wild type and mutant CFTR is notable in two respects. Firstly, the half life of band B is similar for both wild type and mutant versions and secondly, most of the wild type band B appears to be degraded. One interpretation of these results is that synthesis of CFTR involves two steps, retention in the endoplasmic reticulum during which time folding of the protein occurs followed by either export to the Golgi or degradation. Since we detect no difference in the residence time in the endoplasmic reticulum, it would appear that the defect in the case of the non-maturing mutants lies in the second step, that which results in degradation. Furthermore, even wild type seems surprisingly susceptible to degradation since most of band B fails to mature to band C. Whether this results from overexpression of CFTR or is a property of the protein in non-recombinant cells remains to be determined.

Still alternatively, the CFTR protein itself may be responsible for its own exportation out of the endoplasmic reticulum. Under this interpretation, mutant CFTR, or otherwise improperly folded or glycosylated CFTR would not appropriately interact with the endoplasmic reticulum membrane resulting in a self-regulating quality control mechanism having no need of further structures or accessory substances.

A different interpretation of the results would provide that the nascent, incompletely glycosylated CFTR was transported normally to the Golgi but that the structural alterations caused by the various mutations prevented further glycosylation and this lead to lack of activity and eventual degradation. This interpretation is less favored because the previous explanations are more consistent with the present understanding of the intracellular transport of other proteins and their mutant variants (Lodish, 1988; Pelham, 1989; Klausner and Sitia, 1990).

B. Structure:Function of CFTR.

CFTR is a large, complex molecule. Nucleotide binding domain 1 contains two clusters of naturally occuring mutations, one around residue 508 (Riordan et al., 1989, Kerem et al., 1990), the other around 550 (Cutting et al., 1990a; Kerem et al., 1990). All the mutations around 508 disclosed herein (ΔF508, ΔI507, F508R) failed to generate mature CFTR, whereas mutations at the second site, S549I did not produce mature CFTR but G551D did. Mutation of the Walker motif lysine in nucleotide binding domain 1 also prevented maturation of CFTR. The surprising difference between mutations at neighboring residues 549 and 551 is a surprising result. It appears that most of these mutations inactivate some function of the protein, such as its ability to bind nucleotide and maturation of CFTR is prevented by lack of functional activity. More likely, all non-maturing mutants result in structural changes in the domain and these prevent maturation.

Another unexpected result of the experiments disclosed herein is the difference between the modification of the conserved lysine mutants in nucleotide binding domains 1 and 2. K464M did not produce mature CFTR whereas K1250M did. Although the two domains are clearly related and both mutations lie in putative nucleotide binding pockets (Riordan et al., 1989), they appear not to be functionally equivalent.

Mutant R334W (X. Estivill, personal communication) emphasized the importance of the transmembrane domains in the activity of CFTR. The instant disclosure clearly shows that a change in sequence within transmembrane domain 6 does not prevent movement to the Golgi at least as measured by the presence of complex-type N-linked oligosaccharides. Accordingly, the polar amino acid in the otherwise hydrophobic environment plays an important role in pumping material across the membrane.

EXAMPLE 14

Cystic Fibrosis Disease Implications—Diagnosis and Therapy

A. Molecular basis of the disease.

Many genetic diseases are caused by the absence or truncation of the appropriate protein, for example as a result of deletions within the corresponding gene. Muscular dystrophy would be an example in this category (Harper, 1989). Other genetic diseases are caused by mutations that result in loss of function of the gene product. Sickle cell disease is a classic example of this type (Weatherall et al., 1989). One aspect of the instant invention provides that the molecular basis of most cystic fibrosis is the inability of the CFTR gene product to mature. That is to say, the failure of CFTR to move through the normal pathway of intracellular trafficking and modification means that the mature protein is absent from its final cellular destination in CF cells. Examples of genetic lesions that result in failure of the LDL receptor to mature have been described for certain types of familial hypercholesterolemia. In some of these cases, the mutant LDL receptor is retained in the endoplasmic reticulum (Lehrman et al., 1986).

That little or no mature CFTR has been detected in the cells containing CF associated mutations observed in a majority of CF patients does not necessarily mean that this forms the molecular basis of all CF. A priori, it seems very likely that some mutations will inactivate the function of CFTR but will not prevent transport and glycosylation. Indeed, R334W and G551D have been detected in CF chromosomes and presumably encoded inactive CFTR (X. Estivill, personal communication; Kerem et al., 1990). Even so, both encoded CFTR that matures to form band C.

B. Diagnosis.

The mutations described herein represent over 70% of known CF chromosomes (Kerem et al., 1989, 1990; Riordan et al., 1989, Cutting et al., 1990a). Accordingly, the surprising results of the instant invention can be used for purposes of diagnosing CF. Further, it is anticipated that mutations in other CF chromosomes will also fail to produce band C, thus making the detection of CFTR protein in the membrane diagnostic of an even greater percentage of CF. Another aspect of the present invention is the diagnosis of CF by monitoring the presence or absence of mature CFTR. Accordingly, the sensitive detection of band C in primary cells provides a surprisingly useful diagnostic test for detecting the great majority of CF patients.

C. Pancreatic sufficiency and insufficiency.

To date some mutations that cause premature termination of CFTR synthesis appear associated with mild forms of CF, whereas ΔF508 is often associated with severe, pancreatic insufficient forms of the disease (Cutting et al., 1990b). That ΔF508 should be more severe than a major truncation appears counter intuitive. The experimental data disclosed herein support the conclusion that major truncations make no stable CFTR. By contrast, homozygous ΔF508 cells not only make no mature CFTR but worse, they produce mutant protein trapped in the endoplasmic reticulum. Trapped ΔF508 CFTR may retain sufficient activity to cause intracellular pumping of molecules normally transported only at the cell surface. Thus, CFTR activity at the incorrect cellular location would result in effects more serious than those resulting from complete absence of the protein. Accordingly, suitable therapeutic activity would ideally deactivate such inappropriate CRTR activity most preferably, in advance of, or in conjunction with CFTR protein or CFTR gene therapy.

D. Recessive nature of CF.

The absence of mature CFTR encoded by ΔF508 and other similar mutants also provides an explanation for the finding that cells heterozygous for various mutations are apparently wild type in cell surface channel activities associated with CFTR. Previously, it was perhaps surprising that the defective molecule did not interfere with the activity of the wild type. From the instant invention, it was surprisingly discovered that cells heterozygous for ΔF508 completely lack mutant CFTR at the cell surface and in consequence, the wild type protein is able to function uninterruptedly.

E. Therapy.

The instant discovery that the majority of cases of CF are caused by the absence of mature CFTR and possibly, in the case of pancreatic insufficiency, by the additional deleterious effects of incorrectly located, partially active CFTR, confirms the basis of other approaches to CF therapy. For example, drugs active in altering the sub-cellular distribution of proteins could advantageously be used to redistribute to the plasma membrane fully glycosylated mutant forms which retain at least some functional activity. Similarly, agents effective in simulating sufficient CFTR activity to result in export of otherwise mutant CFTR to the Golgi for additional glycosylation could result in improved CFTR function in homozygous CF individuals. Alternatively, therapeutic treatment via a suitable, therapeutically effective blocking agent could be used to deactivate inappropriately located, active, mutant CFTR protein. Alternately, one may promote the transport of such protein to an appropriate location and useful in this regard are reagents active in promoting intracellular transport inhibition. Yet another aspect of the present invention regarding the therapeutic treatment of mislocated CFTR comprises the use of antisense nucleic acid to rid cells of mutant transcript to provide the absence of CFTR which is preferable to incorrectly located protein.

Most preferably, treatment of individuals with CF will comprise the administration of a therapeutically effective amount of replacement CFTR protein. Ideally, the CFTR will be administered via aerosol inhalation so that it is applied directly to the airway cells. The CFTR protein could be formulated in a lipid containing vehicle such as liposomes or in virosomes. The final formulation will advantageously comprise a carrier as a vehicle for physically transporting the CFTR and also ideally chemically stabilizing the CFTR. The most preferred embodiment will also comprise a dissolving agent for dissolving the mucous or otherwise assisting the movement of the CFTR through the mucous layer to the airway cellular membrane. Ideal reagents in this regard would target the CFTR and/or the delivery vehicle to airway cells and further, promote fusion therewith. Reagents active in this manner include viral proteins such as the HA protein (for targeting) and F protein (for fusion) of parainfluenza viruses.

EXAMPLE 15

Formulation of CFTR Protein into Artificial Liposomes

Solubilized preparations of CFTR, whether or not purified, can be reconstituted into artificial liposomes (Klausner et al., in Molecular and Chemical Characterization of Membrane Receptors Alan R Liss N.Y. (1984) p209). Detergent solubilized preparations of CFTR can be added to phospholipid suspensions and the detergent removed, and vesiculation induced either by dialysis (Kagawa Y, Kandrach et al., J. Biol. Chem. 248 676 (1973)), chromatography over Sephadex G50 (Brandt and Ross, J. Biol. Chem. 261 1656 (1986)) or by passing the preparations over Extracti-Gel D (Feder et al., EMBO J. 5 1509 (1986); Cerione et al., J. Biol. Chem. 261 3901 (1986)) or by other methods known to one skilled in the art. For example, for the bovine adenylate cyclase, Smigel (Smigel, J. Biol. Chem. 261 1976 (1986)) found that the cyclase could be reconstituted into liposomes by passing a solution containing CHAPS buffer solubilized cyclase, 1.5 mM phosphatidylethanolamine and 1.0 mM phosphatidylserine over a Sephadex G-50 column. Naturally, obvious experiments also can be carried out to determine the optimal lipid composition of the artificial liposomes needed to achieve fusion or implantation of CFTR into CF cells. In general, membrane proteins orient themselves correctly in liposomes (Klausner et al.). The correct orientation can be determined using antibodies, and if necessary, the separation of correctly-oriented from incorrectly-oriented liposomes can be achieved using immunoaffinity chromatography (Anholt et al., J. Biol. Chem. 256 4377 (1981)).

EXAMPLE 16

Gene Therapy

A genetic therapy approach to treatment of cystic fibrosis would make use of the full length cDNA encoding the CFTR to augment the defective gene and gene product. This approach could entail either introduction of the CFTR cDNA capable of expression of CFTR into human cells in vitro followed by transfer of the cells into the patient or alternatively, one may directly introduce the CFTR cDNA containing vectors into the cystic fibrosis patient. cDNAs recently have been introduced successfully into humans by Rosenberg, Anderson and colleagues (Aebersold et al., J. Cell Biochem. Supplement 14B, 78 (1990)).

Current gene therapy approaches are based on the use of modified retroviral vectors for the introduction of protein coding sequences into cells and animals. For example, using the full length CFTR cDNA of the present invention, similar techniques con be applied to introduce CFTR coding sequences into cystic fibrosis patients.

For example, Lim et al. (Proc. Natl. Acad. Sci. 86 8892 (1989); Mol. Cell. Biol. 7, 359 (1987)) described techniques and vectors for a gene therapy approach to expression in vivo of the human adenosine deamnise gene in hematopoetic stem cells. This system could be easily modified to provide for a gene therapy approach to in vivo expression of the CFTR protein. The work of Rich et al. (1990) and Radmon et al. (Cell 62, 1227 (1990)) confirms the feasibility of this approach.

Additional limitations and criteria regarding the control of CFTR expression following gene therapy will also become apparent upon study of the results of protein production from the various mutants and the manner in which nascent CFTR interacts with the endoplasmic reticulum, transported to Golgi for further carbohydrate processing and subsequent transport to the plasma membrane. Examples 12 and 13 are particularly helpful in this regard.

It is now clear from the present invention that gene replacement therapy for CF will need to control strictly the level of expression of CFTR because overexpression will saturate the transport system involved in maturation. Additionally, CFTR mislocated by over-expression could be as deleterious as protein mislocated by mutation. Accordingly, the protein replacement therapy is preferred since such an approach adntageously avoids this hazard.

EXAMPLE 17

Drug Screening for Pharmacological Agents

A pharmacological approach to develop CF therapies would use cells expressing CFTR from the DNAs of the present invention to screen for and select agents, either natural products, recombinant products or synthesized organic molecules, that could be used therapeutically to compensate for or by-pass the defective CFTR. For example, Ionophores capable of altering membrane conductance or ion channel agonists or antagonist could be potentially useful compounds. Alternatively, agents for mobilizing mutant forms of CFTR to the golgi for glycosylation to partially active CFTR for CF patients could be isolated.

To test for potential pharmaceutical agents, the cell systems of the present invention, either expressing wild-type or mutated forms of CFTR protein from the full length cDNA or isolated DNA sequence encoding CFTR, would be incubated in the presence of varying concentrations of the agent being tested and restoration of the wild-type phenotype or binding of the agent to the cell or CFTR assayed. An example of a suitable assay for testing the restoration of appropriate ion flux, has been described in detail by Mandel, J. Biol. Chem. 261, 704 (1986)and Clancy, Am. J. Physiol., 258 Lung Cell. Physiol. 2 pL25 (1990). Alternatively the detecting step could comprise contacting the cells with a labelled antibody specific for the cystic fibrosis transmembrane conductance regulator and detecting whether the antibody became bound wherein binding is correlated with the presence of an effective agent.

For screening molecules as potential CF therapeutic drug candidates, one could assess the effect of exogenous materials on the function and phenotype of cells expressing either wild-type or defective CFTR. One could examine the $Cl^-$ transport properties as described by Mandel et al. (J Biol Chem 261, 704 (1986)) or one could use the measurement of $^{125}I^-$ efflux (Clancy et al., Am. J. Physiol. 258 Lung Cell. Physiol. 2 pL25 (1990)).

Measurement of $^{125}I^-$ efflux from intact cells provides a relatively easy and fast assay of $Cl^-$ channel activity. $I^-$ is an excellent tracer for $Cl^-$ : It is not secreted across the epithelium (Widdicombe and Welsh, Am. J. Physiol. 239, C112 (1980)) but both the secretagogue-induced apical membrane $Cl^-$ conductance and the outwardly rectifying apical $Cl^-$ channel are more permeable to $I^-$ than to $Cl^-$ (Li and Welsh, Clin. Res. 37, 919a (1989)). Dr. Welsh and colleagues have shown that $^{125}I^-$ efflux: a) is stimulated by an increase in cAMP, by an increase in $Ca^{2+}$, and by cAMP and $Ca^{2+}$ elevating agonists, b) is inhibited by carboxylic acid analogs, c) is not affected by loop diuretics, and d) is voltage-dependent. These data indicate that the $^{125}I^-$ efflux assay measures $Cl^-$ channel activity.

The results of various mutant CFTR expressing cells at 50–75% confluency at ambient $CO_2$ and room temperature (20°–23° C.) is described in prior examples. Cell attached $Cl^-$ channels have a similar function at room temperature and at 37° C. For testing the effect of varying concentrations of substances on the CF phenotype, one could include the substances in the preincubation media and then subsequently conduct efflux measurement assay. Following preincubation one would remove the media, and cells would be washed for 10 seconds in efflux buffer containing (in mM): 135 NaCl, 1.2 $CaCl_2$, 1.2 $MgCl_2$, 2.4 $K_2HPO_4$, 0.6 $KH_2PO_4$, 10 glucose, and 10 HEPES (pH 7.4 with NaOH). Cells would then be loaded with tracer by incubation in buffer containing 15 $\mu Ci/ml$ $^{125}I^-$ for 2–4 hours. Cells then would be washed for 30 sec to remove most non-specifically bound tracer thereby producing a stable baseline rate of efflux. $^{125}I^-$ efflux rates could be measured during a baseline period (5 minutes) and then during stimulation with either cAMP (100 $\mu M$ CPT-cAMP, 10 $\mu M$ forskolin, and 1 mM theophylline) or $Ca^{2+}$ (1 $\mu M$ A23187 or 1 $\mu M$ ionomycin). Measurement of efflux in response to a $Ca^{2+}$ ionophore would provide an important control because an increase in $Ca^{2+}$ activates $Cl^-$ channels in CF cells. Efflux buffer from all time periods plus non-effluxed (lysis) counts would be quantitated in a gamma radiation counter. To increase the utility of this method, the procedure could be adapted to cells grown in 96 well dishes.

Although impractical for wide spread drug screening, in order to further characterize promising candidate molecules, patch clamp studies could be performed on wild-type or mutant CFTR expressing cells. Methods for cell-attached and excised, inside-out patch clamp studies have been described (Li et al., Nature 331, 358 (1988); Welsh, Science 232, 1648 (1986)). $Cl^-$ channels would be identified by their size, selectivity and characteristic outward rectification. With cell attached patches the effect of substances under study could be examined by their addition to the bath. With excised patches the effect of adding substances to the cytosolic surface or external surface of the patch could be determined. Using these assays, promising lead compounds for the treatment of CF could be identified.

It would be advantageous to develop additional rapid assays for monitoring the CFTR protein. Although the exact function of the CFTR protein is not known, the presence of nucleotide binding domains of other proteins suggests that the CFTR may react with radiolabeled nucleotide analogues or could hydrolyze nucleotide triphosphates. For example, attempts to photoaffinity label CFTR with 8-azido-$\alpha$-($^{32}P$) ATP could follow the basic protocol of Hobson et al. (Hobson et al., Proc. Natl. Acad. Sci. 81 7333, (1984)) as successfully modified for labeling of the multi-drug resistance, P glycoprotein (Cornwall et al., FASEB J 1, 51 (1987)). Membrane vesicles from cells or solubilized micelles could be incubated in HEPES buffered mannitol with $MnCl_2$, $MgCl_2$ and photoaffinity label. Samples would be irradiated at 366 nm and then either electrophoresed directly on SDS gels to determine the extent of labeling or immunoprecipitated to quantitate label incorporated into CFTR.

Additionally, one could advantageously attempt to measure ATP hydrolysis by modification of the procedure used by Hamada and Tsuro for measuring the ATPase activity of P-glycoprotein (Hamada and Tsuro, J Biol Chem 263 1454, (1988)). CFTR could be solubilized as disclosed and immunoprecipitated by reaction with antibody and then protein A-Sepharose followed by incubation in the presence of ($\alpha$-$^{32}P$)ATP. The reaction would be stopped by the addition of EDTA and excess nonradioactive ATP and ADP. The reaction products would be separated by chromatography on polyethyleneimine-cellulose thin layer plates, the ADP-containing spots detected by UV light and quantitated (Cerenkov). Qualitative hydrolysis could be determined by autoradiography of the TLC plate. In drug screening, the effect of varying concentrations of added substances on these assays could be determined and molecules with potential as CF therapeutics identified.

Those skilled in the art will now recognize that numerous variations and modifications of the foregoing may be made without departing from either the spirit or scope of the present invention. For example, many expression systems utilizing different vectors and/or different host cells may be employed in substitution of those described herein to produce CFTR. Further, minor modifications of the cDNA sequence provided here, or the substitution of different stabilizing introns in different locations can be made without altering functional characteristics of the CFTR protein and are thus to be deemed equivalents of the inventions disclosed herein. Given the broad nature of the diagnostic and therapeutic aspects of the present invention, obvious amendments thereto, derivations therefrom and modifications thereof may be made without departing from the scope of the inventive contributions made herein.

REFERENCES

Boat, T., Welsh, M. J., and Beaudet, A. (1989). Cystic fibrosis, in: The Metabolic Basis of Inherited Disease, C. Scriver, A. Beaudet, W. Sly, and D. Valle, eds. (McGraw Hill, New York), pp. 2649–2860.

Cheng, S. H., Harvey, R., Espino, P. C., Semba, K., Yamamoto, T., Toyoshima, K. and Smith, A. E. (1988). Peptide antibodies to the human c-fyn gene product demonstrate pp59$^{c-fyn}$ is capable of complex formation with the middle-T antigen of polyomavirus. EMBO J. 5, 325–334.

Cleveland, D. W., Fischer, S. G., Kirschner, M. W. and Laemmli, U.K. (1977). Peptide mapping by limited proteolysis in sodium dodecyl sulfate and analysis by gel electrophoresis. J. Biol. Chem. 252, 1102–1106.

Cohen, S. N., Chang, A. C. Y., Boyer, H. W., and Helling, R. B. (1973). Construction of biologically functional bacterial plasmids in vitro. Proc. Natl. Acad. Sci. USA 70, 3240–3244.

Cutting, G. R., Kasch, L. M., Rosenstein, B. J., Zielenski, J. Tsui, L. -C., Antonarakis, S. E. and Kazanian, H. H.,Jr. (1990a). A cluster of cystic fibrosis mutations in the first nucleotide binding fold of the cystic fibrosis conductance regulator protein. Nature 346, 366–369.

Cutting, G. R., Kasch, L. M., Rosenstein, B. J., Tsui, L.-C., Kazazian, H. H.,Jr. and Antonarakis, S. E. (1990b). Two cystic fibrosis patients with mild pulmonary disease and nonsense mutations in each CFTR gene. Am. J. Hum. Genet. 47, 213.

Dean, M., White, M. B., Amos, J., Gerrard, B., Stewart, C., OSKhaw, K. -T., and Leppart, M. (1990) Multiple mutations in highly conserved residues are found in mildly affected cystic fibrosis patients. Cell 61, 863–870.

Drumm, M. L., Pope, H. A., Cliff, W. H., Rommens, J. M., Marvin, S. A., Tsui, L. -C., Collins, F. S., Frizzel, R. A., and Wilson, J. M. (1990) Correction of the cystic fibrosis defect in vitro by retrovirus-mediated gene transfer. Cell 62, 1227–1233.

Frizzell, R. A., Rechkemmer, G. and Shoemaker, R. L. (1986). Altered regulation of airway epithelial cell chloride channels in cystic fibrosis. Science 233; 558–560.

Gregory, R. J., Cheng, S. H., Rich, D. P., Marshall, J., Paul, S., Hehir, K., Ostedgaard, L., Klinger, K. W., Welsh, M. J., and Smith, A. E. (1990). Expression and characterization of the cystic fibrosis transmembrane conductance regulator. Nature 347, 382–386.

Harlow, E., Crawford, L. V., Pim, D. C., and Williamson, N. M. (1981). Monoclonal antibodies specific for simian virus 40 tumor antigens. J. Virol. 39, 861–869.

Harper, P. S. (1989). The muscular dystrophies. In: The Metabolic Basis of Inherited Disease, C. Scriver, A. Beaudet, W. Sly, and D. Valle, eds. (McGraw Hill, New York), pp. 2869–2904.

Hurtley, S. M., and Helenius, A., (1989). Protein oligomerization in the endoplasmic reticulum. Ann. Rev. Cell Biol. 5, 377–307.

Hyde, S. C, Emsley, P. Hartshorn, M. J. Mimmack, M. M. Gileadi, U., Pearce, S. R., Gallagher, M. P., Gill, D. R., Hubbard, R. E., and Higgins, C. F. (1990). Structural model of the ATP-binding proteins associated with cystic fibrosis, multidrug resistance and bacterial transport. Nature 346, 362–365.

Hwang, T. -C., Lo, L., Zeitlin, P. L., Gruenert, D. C., Huganir, R., Guggino, W. B, (1989)_. Ce-channels on CF: Lack of Activation by Protein Kinase C and cAMP-Dependent Protein Kinase, Science 244,1351–3.

Kaideron, D., Richardson, W. D., Markham, A. F. and Smith, A. E. (1985). Sequence requirements for nuclear location of simian virus 40 large-T antigen. Nature 311, 33–38.

Kerem, B. -S., Rommens, J. M., Buchanan, J. A., Markiewicz, D., Cox, T. K., Chakravarti, A., Buchwald, M., and Tsui, L. -C. (1989) Identification of the cystic fibrosis gene: genetic analysis. Science 245, 1073–1080.

Kerem, B. -S., Zielenski, J., Markiewicz, D., Bozon, D., Gazit, E., Yahaf, J., Kennedy, D., Riordan, J. R., Collins, F. S., Rommens, J. R., and Tsui, L. -C. (1990). Identification of mutations in regions corresponding to the two putative nucleotide (ATP)-binding folds of the cystic fibrosis gene.Proc. Natl. Acad. Sci. USA 87, 8447–8451.

Klausner, R. D., and Sitia, R. (1990) Protein degradation in the endoplasmic reticulum. Cell 62, 611–614.

Kunkel, T. M. (1985). Rapid and efficient site-specific mutagenesis without phenotypic selection. Proc. Natl. Acad. Sci. USA 82, 488–492.

Laemmli, U. K. (1970). Cleavage of structural proteins during assembly of the head of bacteriophage T4. Nature 227, 680–685.

Lehrman, M. A., Schneider, W. J., Brown, M. S., Davis, C. G., Elhammer, A., Russell, D. W., and Goldstein, J. L. (1986). The Lebanese allele at the low density lipoprotein receptor locus. Nonsense mutation produces truncated receptor that is retained in endoplasmic reticulum. J. Biol. Chem. 262, 401–410.

Li, M., McCann, J. D., Liedtke, C. M., Nairn, A. C., Greengard, P. and Welsh, M. J. (1988). Cyclic AMP-dependent protein kinase opens chloride channels in normal but not cystic fibrosis airway epithelium. Nature 331, 358–360.

Li M., McCann, J. D., Anderson, M. P., Clancy, J. P., Liedtke, C. M., Nairn, A. C., Greengard, P. and Welsh, M. J. (1989). Regulation of Chloride Channels by Protein Kinase C in Normal and Cystic Fibrosis Airway Epithelia. Science 244, 1353–1356.

Lodish, H. F. (1988). Transport of secretory and membrane glycoproteins from the rough endoplasmic reticulum to the golgi. J. Biol. Chem. 263, 2107–2110.

Pelham, H. R. B. (1989). Control of protein exit from the endoplasmic reticulum. Ann. Rev. Cell Biol. 5, 1–23.

Quinton, P. M. (1989). Defective epithelial ion transport in cystic fibrosis. Clin. Chem. 35, 726–730.

Rich, D. P., Anderson, M. P., Gregory, R. J., Cheng, S. H., Paul, S., Jefferson, D. M., McCann, J. D., Klinger, K. W., Smtih, A. E., and Welsh, M. J. (1990). Expression of the cystic fibrosis transmembrane conductance regulator corrects defective chloride channel regulation in cystic fibrosis airway epithelial cells. Nature 347, 358–363.

Riordan, J. Rommens, J. M., Kerem, B. -S., Alon, N., Rozmahel, R., Grzelczack, Z., Zielenski, J., Lok, S., Plavsic, N., Chou, J. -L., Drumm, M. L., Iannuzzi, M. C., Collins, F. S., and Tsui, L. -C. (1989). Identification of the cystic fibrosis gene: cloning and characterization of the complementary DNA. Science 245, 1066–1073.

Rommens, J. H., Iannuzzi, M. C., Kerem, B. -S., Drumm, M. L., Melmer, G., Dean, M., Rozmahel, R., Cole, J. L., Kennedy, D., Hidaka, N., Zsiga, M., Buchwald, M., Riordan, J. R., Tsui, L. -C., and Collins, F. S. (1989). Identification of the cystic fibrosis gene:chromosome walking and jumping. Science 245, 1059–1065.

Rose, J. K., and Doms, R. W. (1988) Regulation of protein export from the endoplasmic reticulum. Ann. Rev. Cell. Biol. 4, 257–288.

Sambrook, J., Fritsch, E. F., and Maniatis, T. (1989). Molecular Cloning: A Laboratory Manual (Cold Spring Harbor, New York: Cold Spring Harbor Laboratory).

Weatherall, D. S., Clegg, J. B., and Wood, W. G. (1989). The hemaglobinopathies. In: The Metabolic Basis of inherited Disease, C. Scriver, A. Beaudet, W. Sly, and D. Valle, eds. (McGraw Hill, New York), pp. 2281–2340.

Welsh, M. J. (1986). An apical-membrane chloride channel in human tracheal epithelium. Science 232, 1648–1650.

Welsh M. J. and Liedtke, C. M. (1986). Chloride and Potassium Channels in Cystic Fibrosis Airway Epithelia Nature, 322, 467.

TABLE 1

| Mutant | CF | Exon | CFTR Domain | A | B | C |
| --- | --- | --- | --- | --- | --- | --- |
| Wild Type | | | | − | + | ++ |
| R334W | Y | 7 | TM6 | − | + | ++ |
| K464M | N | 9 | NBD1 | − | + | − |
| ΔI507 | Y | 10 | NBD1 | − | + | − |
| ΔF508 | Y | 10 | NBD1 | − | + | − |
| F508R | N | 10 | NBD1 | − | + | − |
| S549I | Y | 11 | NBD1 | − | + | − |
| G551D | Y | 11 | NBD1 | − | + | ++ |
| N894,900Q | N | 15 | ECD4 | + | − | − |
| K1250M | N | 20 | NBD2 | − | + | ++ |
| Tth111 I | N | 22 | NBD2-Term | − | + | − |

What is claimed:

1. A method of producing a DNA molecule encoding wild type human cystic fibrosis transmembrane conductance regulator protein (CFTR), said method comprising:
growing E. coli cells comprising a purified and isolated DNA molecule encoding wild type human CFTR; and recovering said DNA from said cells.

2. The method of claim 1 wherein the E. coli further comprises a regulatory element operably linked to the DNA molecule encoding wild type CFTR, said regulatory element capable of replication in E. coli.

3. The method of claim 1, wherein the DNA molecule encodes the complete CFTR protein whose amino acid sequence is set forth in FIGS. 14A–14G.

4. The method of claim 1, wherein the DNA molecule is a cDNA.

5. A method of producing a DNA molecule encoding wild type human CFTR, said method comprising:

growing host cells comprising a purified and isolated DNA molecule encoding wild type human CFTR, wherein the DNA molecule is capable of stable propagation in *E. coli* cells; and recovering said DNA from the host cells.

6. The method of claim 5 wherein the host cells further comprise a regulatory element operably lined to the DNA molecule, said regulatory element capable of replication in the host cells.

7. The method of claim 5, wherein the DNA molecule encodes the complete CFTR protein whose amino acid sequence is set forth in FIG. 14.

8. The method of claim 5, wherein the DNA molecule is a cDNA.

* * * * *